(12) United States Patent
Plachta et al.

(10) Patent No.: US 11,224,749 B2
(45) Date of Patent: Jan. 18, 2022

(54) IMPLANTABLE ASSEMBLY

(71) Applicant: Neuroloop GmbH, Freiburg (DE)

(72) Inventors: Dennis Plachta, Voerstetten (DE);
Mortimer Giehrtmuehlen, Freiburg (DE); Thomas Stieglitz, Freiburg (DE); Josef Zentner, Freiburg (DE)

(73) Assignee: NEUROLOOP GMBH, Freiburg (DE)

( * ) Notice: Subject to any disclaimer, the term of this patent is extended or adjusted under 35 U.S.C. 154(b) by 56 days.

(21) Appl. No.: 16/743,065

(22) Filed: Jan. 15, 2020

(65) Prior Publication Data
US 2020/0147394 A1     May 14, 2020

Related U.S. Application Data

(62) Division of application No. 15/517,922, filed as application No. PCT/EP2015/073131 on Oct. 7, 2015, now Pat. No. 10,556,111.

(51) Int. Cl.
*A61N 1/36*     (2006.01)
*A61N 1/372*    (2006.01)
(Continued)

(52) U.S. Cl.
CPC ...... *A61N 1/36175* (2013.01); *A61N 1/36117* (2013.01); *A61N 1/36139* (2013.01);
(Continued)

(58) Field of Classification Search
CPC ............ A61N 1/36175; A61N 1/36117; A61N 1/36139; A61N 1/372; A61N 1/0504; A61N 1/0556; A61N 1/36125
See application file for complete search history.

(56) References Cited

U.S. PATENT DOCUMENTS 5,919,220 A       7/1999  Stieglitz et al.
2003/0236557 A1*  12/2003 Whitehurst ........ A61N 1/37205
                                                 607/39
(Continued)

FOREIGN PATENT DOCUMENTS

DE    44 33 111 A1    3/1996
DE    100 28 522 A1   12/2001

OTHER PUBLICATIONS

International Search Report for PCT/EP2015/073131 dated Jan. 22, 2016; English translation submitted herewith (9 pages).
(Continued)

*Primary Examiner* — Catherine M Voorhees
*Assistant Examiner* — Roland Dinga
(74) *Attorney, Agent, or Firm* — Fitch, Even, Tabin & Flannery LLP

(57) ABSTRACT

An implantable assembly is described for acquisition of neuronal electrical signals at a selected location which propagate along at least one nerve fiber contained in a nerve fiber bundle, as well as for selective electrical stimulation of the at least one nerve fiber, having: an implantable electrode assembly (E) which is disposed on a biocompatible support substrate which can be positioned around the nerve fiber bundle in a cuff. The cuff has a cylindrical support substrate surface (i) which in the implanted condition is orientated facing the nerve fiber bundle, on which a first electrode assembly for locationally selective acquisition of the neuronal electrical signals and selective electrical stimulation of the at least one nerve fiber, and on which a second electrode assembly is disposed to record an ECG signal, and an analysis and control unit (A/S) which can be electrically conductively connected or is connected to the implantable electrode assembly (E), in which the locationally selective acquired neuronal electrical signals as well as the ECG signal can be analyzed in a time-resolved manner such that
(Continued)

a neuronal time signal correlated with a physiological parameter, such as blood pressure, can be derived.

1 Claim, 11 Drawing Sheets

(51) Int. Cl.
*A61N 1/378* (2006.01)
*A61N 1/05* (2006.01)

(52) U.S. Cl.
CPC ........... *A61N 1/372* (2013.01); *A61N 1/3782* (2013.01); *A61N 1/0504* (2013.01); *A61N 1/0556* (2013.01); *A61N 1/36125* (2013.01)

(56) References Cited

U.S. PATENT DOCUMENTS

| | | |
|---|---|---|
| 2006/0122675 A1 | 6/2006 | Libbus et al. |
| 2010/0204741 A1 | 8/2010 | Tweden et al. |
| 2011/0301659 A1 | 12/2011 | Yoo et al. |
| 2014/0135645 A9 | 5/2014 | Wenzel et al. |

OTHER PUBLICATIONS

Written Opinion of the International Searching Authority or PCT/EP2015/073131 dated Jan. 22, 2016; English translation submitted herewith (13 pages).

\* cited by examiner

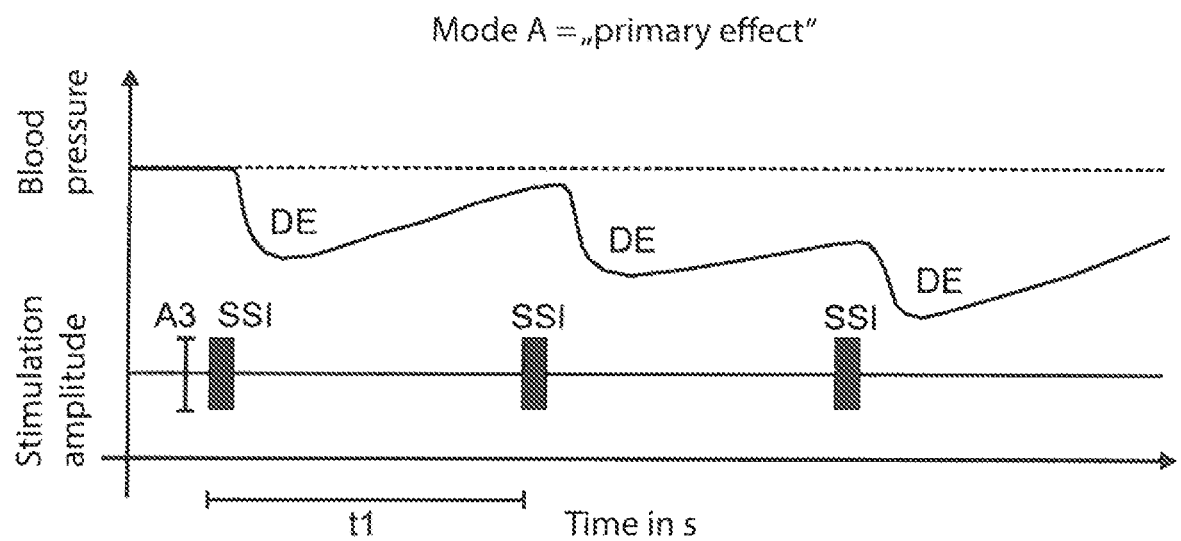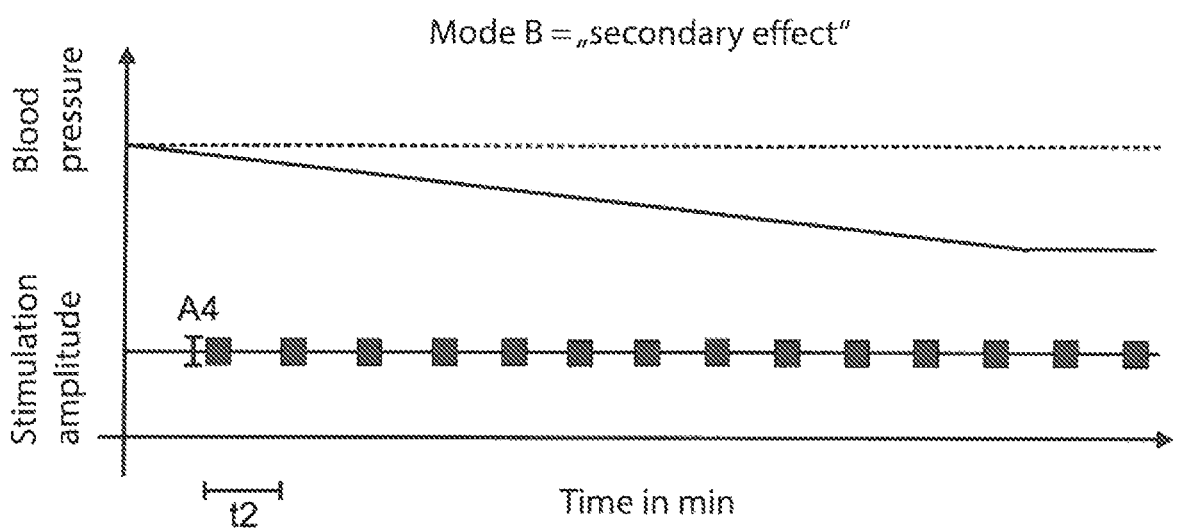
Fig. 5

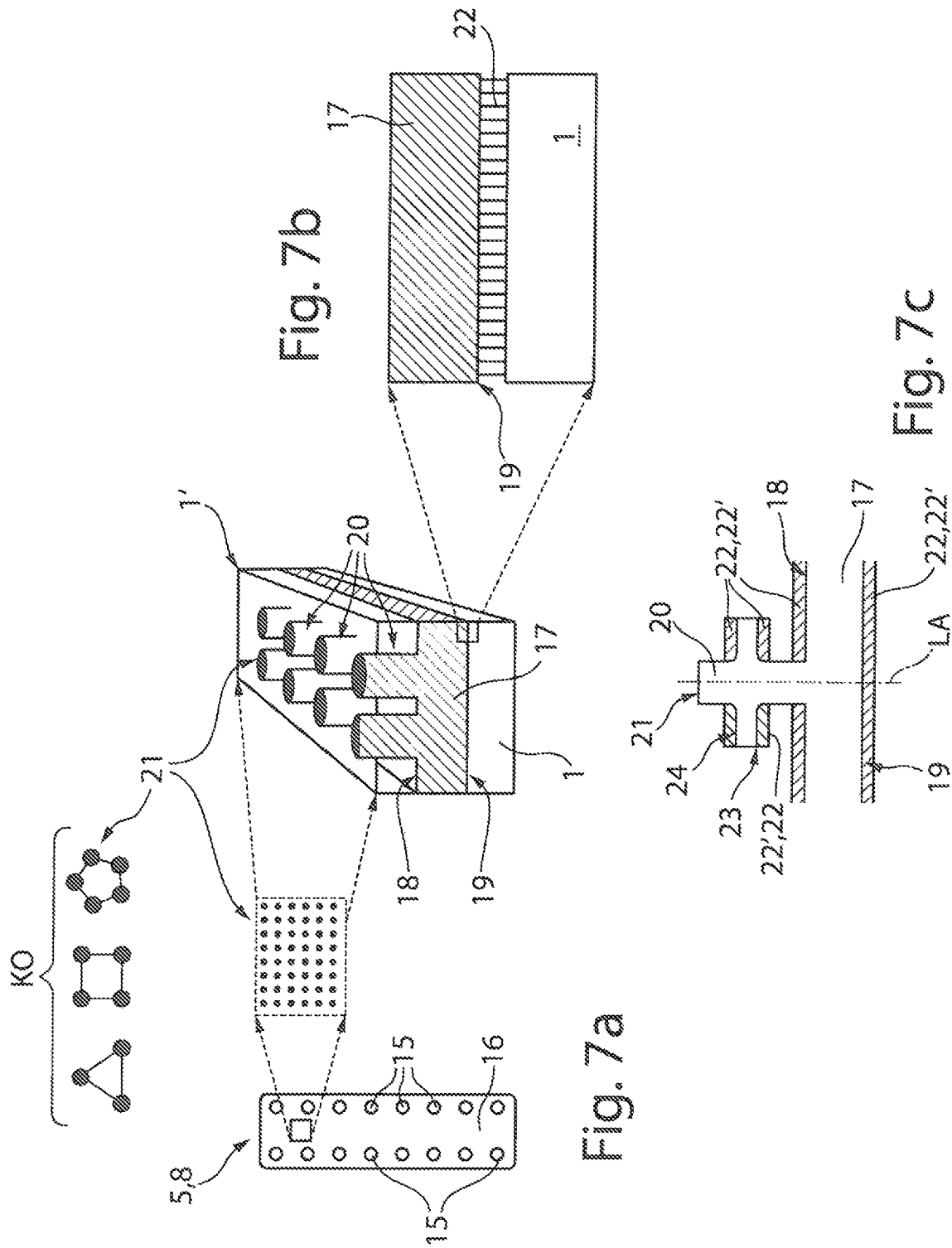

IMPLANTABLE ASSEMBLY

CROSS-REFERENCE TO RELATED APPLICATIONS

This application is a divisional of U.S. patent application Ser. No. 15/517,922, filed Apr. 7, 2017, which is a U.S. National Stage Entry of International Application No. PCT/EP2015/073131 filed Oct. 7, 2015, which claims priority from German Patent Application No. 10 2014 014 942.0, filed Oct. 7, 2014, which are hereby incorporated herein by reference in their entirety.

BACKGROUND OF THE INVENTION

Technical Field

The invention relates to an implantable assembly for locationally selective acquisition of neuronal electrical signals which propagate along at least one nerve fiber contained in a nerve fiber bundle, as well as to selective electrical stimulation of the at least one nerve fiber. The implantable assembly comprises an implantable electrode assembly which can be positioned around a nerve fiber bundle in a cuff, by which electrical signals can be applied to selected nerve fibers within the nerve fiber bundle. The electrical stimulation is in particular carried out by specifically manipulating the blood pressure in an animal or human patient.

Description of the Prior Art

Arterial hypertension is a global and typical disease of civilization which threatens the lives of millions of patients and at the same time places a huge burden on the health services. Therapeutic measures until now have been based on the administration of blood pressure-reducing medication such as ACE inhibitors, beta blockers, etc., but in addition to the desired blood pressure-reducing effect, they are associated with substantial side effects such as, for example, bradycardia, heart failure, asthma attacks, etc. In addition, despite the development of new blood pressure-reducing drugs, in up to 30% of all patients taking similar medication, a sufficient target blood pressure cannot be obtained. See the paper by H R Black et al., "Principal Results of the Controlled Onset Verapamil Investigation of Cardiovascular End Points (Convince)", TRIAL, Jama, 289 (16), pp 2073-2082, 2003.

A further therapeutic approach to combatting high blood pressure follows on from a study by the Applicant which has been published in the article by Dennis T T Plachta, Oscar Cota, Thomas Stieglitz, Mortimer Gierthmuehlen, "Selektive Ableitung und Stimulation für ein blutdrucksenkendes Implantat unter Verwendung von Vielkanal-Cuff-Elektroden" [Selective Recording and Stimulation for a Blood Pressure-Reducing Implant Using Multi-Channel Cuff Electrodes], tm—Technisches Messen, 2013, vol 80 (5), pp 163-172. The results obtained by animal tests carried out on rats give rise to the possibility of detecting neuronal electrical signals in a locationally resolved manner from the nerve fiber bundle section by an electrode assembly implanted on a nerve fiber bundle section of the vagus nerve, as well as applying electrical signals to selected nerve fibers to stimulate them for the purposes of a technologically initiated blood pressure reduction. Stimulation of the vagus nerve of this type thus in principle has the potential of becoming an alternative treatment for therapy-refractory blood pressure.

The concept of selective vagus nerve stimulation is based on many years' experience in applying and establishing neuromodulatory therapy of severe forms of epilepsy, in which the vagus nerve is electrically stimulated in its entirety with the aid of an implanted electrode assembly in order to mitigate at least their extent as regarding severity and duration of incipient epileptic episodes. In this regard see F Sidiqui et al. "Cumulative Effect of Yagus Nerve Stimulators on Intractable Seizures Observed Over a Period of 3 Years", Epilepsy and Behavior, 18(3), pp 299-302, 2010, as well as T Stieglitz, "Neuroprothetik und Neuromodulation-Forschungsansatze und klinische Praxis bei Therapie und Rehabilitation" [Neuroprosthetics and neuromodulation—research strategies and clinical practice in therapy and rehabilitation], Bundesgesundheitsblatt-Gesundheitsforschung-Gesundheitsschutz, 53(8), pp 783-790, 2010.

In contrast, for the chronic treatment of hypertension, the fibers relevant to blood pressure initially have to be located metrologically in order to then selectively electrically stimulate them in a particular manner. In order to protect the vagus nerve as far as possible from the positioning of an electrode assembly by implantation and in order to irritate the epineurium of the vagus nerve as little as possible, in the cited contribution by Dennis T T Plachta et al., the use of what is known as a cuff electrode is proposed which can be extraneurally attached to the vagus nerve. This has the advantage that the cuff electrode is relatively easy to position along the vagus nerve and, moreover, means that surgical intervention is only slightly invasive for a patient and thus goes easy on the patient and is also rapid to carry out.

The baroreflex acts to regulate blood pressure naturally; it constitutes a homeostatic, self-regulating mechanism and reflexively activates various effectors in the event of an elevated blood pressure. The heart rate is reduced, inter alia, as well as dilating the arterial vessels in order to reduce the blood pressure. In the case of a low blood pressure, the baroreflex is suppressed, whereupon the heart rate rises and blood vessels are constricted so that the blood pressure rises once again. The sensory inputs for the baroreflex are known as baroreceptors which, inter alia, are located in the walls of the aortic arch. From here, the blood pressure information runs monosynaptically along the nerve fibers relevant to blood pressure, hereinafter termed baroreceptive fibers, to the brain stem. When a threshold for the blood pressure is exceeded, the baroreflex triggers inhibition of sympathetic nerve fibers, leading to an immediate drop in the blood pressure. With the aid of the cuff electrode shown here in FIGS. 2a and 2b, it is possible to exploit this baroreflex mechanism by selectively detecting the pressure information supplied to the brain stem and simultaneously selectively "overwriting" it in order in this manner to suggest a substantially increased blood pressure situation to the brain stem, whereupon a natural significant drop in blood pressure is initiated.

FIG. 2a shows the known cuff electrode E in a planar view, in a planar unfolded state. FIG. 2b shows the cuff electrode E when implanted, in which regions B1 and B2 of the cuff electrode E have been folded on top of each other in order to save space and, moreover, a support substrate region 1B of the cuff electrode E provided with a first electrode assembly 2 surrounds a region of the nerve fiber bundle NFB in a cuff.

The cuff electrode E consists of a flexible, biocompatible support substrate 1 which in the embodiment shown is a polyimide film approximately 11 µm thick on which is positioned, on the top of the support substrate facing the plane of the drawing in FIG. 2a, a first electrode assembly 2 composed of a plurality of individual electrodes for the purposes of spatially resolved acquisition of neuronal electrical signals as well as for selective electrical stimulation of individual nerve fibers NF running in the nerve fiber bundle NFB. The individual electrodes of the first electrode assembly 2 come into direct superficial contact with the epineurium EPI of the nerve fiber bundle NFB because, by appropriate application of mechanical pretensioning, the support substrate 1 in the support substrate region 1B has rolled itself up, forming a support substrate surface 1' in the form of a right cylinder facing the nerve fiber bundle NFB, as can be seen in FIG. 2b. In this manner, the individual electrodes of the first electrode assembly 2 assume an annular shape in space in the circumferential direction U curved around the nerve fiber bundle NFB.

Both for locationally selective acquisition of neuronal electrical signals and also for selective electrical stimulation of at least one nerve fiber NF, three first electrode structures 3 are provided which are each disposed at equal axial distances from each other which comprise, in the circumferential direction U, at least two electrode contacts 4, or eight as illustrated in the embodiment of FIG. 2a, b. The respective eight first electrode contacts 4 belonging to a first electrode structure 3 are disposed evenly in the circumferential direction U, that is at 450 with respect to each other. This enables eight-fold locational selectivity in the circumferential direction for locationally selective acquisition of neuronal electrical signals from the nerve fiber bundle NFB to be investigated. The first electrode strips 5 disposed respectively axially on both sides next to the three first electrode structures 3, which completely surround the nerve fiber bundle NFB, act as a ground potential in the event of locationally selective acquisition of neuronal electrical signals. However, if selectively targeted nerve fibers NF within the nerve fiber bundle NFB are to be stimulated electrically, then these first electrode strips 5 each act as an anode or as a counter-pole.

The threefold or tripolar disposition of the respective first electrode structures 3, by means of which respective first electrode contacts 4 acquire monopolar neuronal electrical signals, or electrical signals can be emitted for the purposes of locationally selective stimulation, allows impedance changes due to tissue growth at the metallic electrode contacts 4 to be determined and to be eliminated by the processing technology; on the other hand, neuronal signals relevant to blood pressure which run through the tripole assembly axially along an appropriate nerve fiber NF with a slight time delay, can be detected by means of appropriate tripolar amplification. In addition to the first electrode structures 3 described above as well as first electrode strips 5 which each assume a circular shape, which are all are positioned on the support substrate surface 1' facing the plane of the drawing in FIG. 2a and which end proximally in connection structures V via corresponding electrical lines L, a second electrode assembly in the form of reference electrodes 12 is positioned on the rear of the support substrate 1 which on the one hand serves to acquire the intracorporeal electrical background ground signal or noise level which is at the basis of the signal analysis, on the other hand allows ECG signals to be acquired with the aid of the cuff electrode E. The electrode assembly which can be implanted as a cuff electrode can be connected, via the electrical connection structures V, with a hermetically encapsulated signal detector and generator 6 which is also configured as an implant.

With the known implantable electrode assembly, in the context of animal experiments on rats, it has been shown that with the aid of the total of 24 first electrode contacts distributed evenly around the nerve fiber bundle NFB as tripoles, blood pressure-correlated neuronal electrical time signals, hereinafter termed baroreceptive signals, can be acquired which furthermore, because their signal level is a function of circumferential direction, can act to localize the baroreceptive nerve fibers. Stimulation is tripolar, with that electrode contact 4 or those electrode contacts 4 of the centrally disposed first electrode structure 3 of the tripole assembly being used to detect the respective largest signal level of the baroreceptive signals. It has been shown that, by means of selective stimulation of baroreceptive nerve fibers, the blood pressure can be reduced reliably and significantly, wherein only very slight bradycardia (pulse reduction below 60 beats per minute) as well as barely noticeable bradypnoea (slowing of breathing to less than 20 breaths per minute) occurred.

In order to selectively electrically stimulate the baroreceptive nerve fibers, electrical stimulation signals were applied, on the basis of a specific combination of fixed predetermined stimulation parameters, to the respective selected electrode contacts 4 of the centrally disposed electrode structure. In this regard, the stimulation signals in the form of electrical stimulation events were applied to the selected nerve fibers at freely selectable intervals; as an example, every 20 seconds an electrical stimulus composed of 100 individual pulses was applied to the nerve fiber bundle via the respective selected electrode contact(s). Each individual pulse in this respect had a stimulation pulse duration of 0.6 ms with an anodic or cathodic stimulation amplitude of 0.8 mA respectively, whereupon electrode polarization was made possible. With a repetition rate for the individual pulse, what is known as the stimulation frequency, of 40 Hz, the total duration of an individual electrical stimulus was 100×25 ms, i.e. 2.5 seconds. In the stimulation experiments carried out on rats, different respective predetermined stimulation parameters were employed, namely a respective stimulation frequency of 30 to 50 Hz, a stimulation pulse duration of 0.1 ms to 0.5 ms as well as a stimulation amplitude of 0.3 mA to 1.5 mA.

However, although the knowledge gained in the context of the previous animal experiments regarding manipulating the blood pressure by selective electrical stimulation of baroreceptive nerve fibers appears to be highly promising, at least the quantitative relationships between the electrical stimulation event and the biological response in the form of a drop in blood pressure initiated on the basis of an organic regulation mechanism is still poorly understood. Particularly with larger animals than the rats used in animal experiments until now, or indeed in humans, far more regulatory stimulations have to be carried out beforehand in order to arrive at an outcome for organic regulation which is within a quantitatively determined range of tolerances.

SUMMARY OF THE INVENTION

The object of the invention is an improved implantable assembly for locationally selective acquisition of neuronal electrical signals which propagate along at least one nerve fiber contained in a nerve fiber bundle, and for selective electrical stimulation of at least one nerve fiber with an electrode assembly as described here, in a manner such that the stimulative manipulation of specific regions of the vegetative nervous system, in particular the vagus nerve, can be undertaken with significantly greater precision for the purposes of manipulating blood pressure. When considering carrying out such regulative measures on larger life forms than rats, in particular on humans, it must be ensured that the desired neuronal, physiological and/or organic state is established within at least a foreseeable quantifiable range of tolerances. All of the measures required in this regard should also exclude undesirable biological side effects. In principle, in addition to the desired manipulating of the blood pressure, as an alternative or in combination, the assembly should also be applicable to any other vegetative but also sensorimotoric parameters for the purposes of specific manipulation.

In contrast to the procedure described above for electrical stimulation of at least one selected nerve fiber with respectively rigidly fixed stimulation parameters, that is stimulation pulse duration, stimulation amplitude and stimulation frequency, the implantable assembly configured in accordance with the invention enables electrical stimulation signals to be produced in the form having a temporal amplitude profile in a pulse wave form, which is broadly comparable to natural blood pressure signals and also is to be temporally overlaid with the natural blood pressure signals at the baroreceptive nerve fibers, so that the natural blood pressure signals transmitted along the baroreceptive nerve fibers from the baroreceptors to the brain stem can be overwritten properly. In this manner, unlike as before, the stimulation in accordance with the invention does not follow a pulsating "on-off-on-off" pattern, but instead the engineered electrical stimulation signals applied along the baroreceptive nerve fibers are supplied to the brain stem with a stimulation frequency which matches the natural signal rhythm, that is respectively in the natural time window in which the brain stem expects the blood pressure signals.

The natural form of a pulse wave which runs through the baroreceptive fields in the aortic arch typically has a pulse duration of less than one second and moreover is characterized by a strong, fast and non-linear pulse wave rise and a subsequent slow fall, which is also non-linear. This mechanical pulse wave is transduced by the baroreceptors into a neuronal electrical signal form. This neuronal electrical signal is fed to the brain stem via the vagus nerve and contains the information regarding the strength and duration of the mechanical pulse wave. By matching this natural neuronal electrical signal form, manipulation of the natural organic regulation mechanism engineered by the implantable assembly is carried out by temporally coherently overwriting the natural neuronal electrical time signal with engineered electrical stimulation signals applied to the at least one selected baroreceptive nerve fiber the amplitude level of which is above or below the natural neuronal electrical time signals, depending on the desired therapeutic outcome. In this manner, the natural, organic blood pressure regulation mechanism is not irritated or is not significantly irritated, that is the brain stem which receives the technically manipulated electrical stimulation signals cannot discern any difference with respect to the natural neuronal electrical time signals. As a result, the natural organic regulation mechanism is activated, leading in a completely natural manner to a regulation outcome which is in the form of a specific and expected adjustment in blood pressure.

Furthermore, the implantable assembly in accordance with the invention offers the possibility of autonomous control of blood pressure monitoring, that is the natural organic regulation mechanism is only activated in those events in which a significant departure from a normal blood pressure is observed. More advantageously, it is possible to operate the implantable assembly by self-control, that is in the manner of a closed loop function, in which the organic regulation outcome brought about by an electrical stimulation acquires, analyses and, if necessary, undertakes appropriate subsequent regulation.

In this regard, the implantable assembly in accordance with the invention for locationally selective acquisition of neuronal electric signals which propagate along at least one nerve fiber contained in a nerve fiber bundle, preferably a baroreceptive fiber, and also for selective electrical stimulation of the at least one nerve fiber, is characterized by the following components:

The assembly in accordance with the invention will now be described by way of an example of manipulating blood pressure as the physiological parameter, without limitation to the general inventive concept. Clearly, the implantable assembly may also be used to manipulate other physiological parameters, for example breathing rate, heart rate, body temperature, etc., or other clinical pictures, for example autoimmune diseases, heart rhythm problems, severe depression, epilepsy, etc. The implantable assembly can be used for the therapy of alternative body functions as well as other peripheral nerves or nerves of the central or vegetative nervous system. An example is the field of motor neuroprostheses following central paralysis as a consequence of spinal or brain injuries. In these cases, the sensory signals from the pressure and location receptors of the hand, for example, can be selectively attached to implantable assemblies and the grip strength can be self-regulated in accordance with a set point setting. In the field of neuromodulation, the implantable assembly may also be envisaged in rehabilitation following stroke and hemiparesis. In this regard, the sensory signal can be amplified and coupled to improve the outcome of rehabilitation. It is also possible to envisage a controlled breath stimulator employing the implantable assembly, via the phrenic nerve to the diaphragm, modulation of the sympathetic nervous system on the sympathetic trunk or efficient pain therapy by means of highly selective peripheral nerve stimulation.

For the purposes of locationally selective acquisition of neuronal electrical signals along selected nerve fibers within a nerve fiber bundle as well as for selective electrical stimulation of the at least one selected nerve fiber, an implantable electrode assembly is provided which is positioned on a biocompatible support substrate which can be placed around the nerve fiber bundle in a cuff which has a right cylindrical support substrate surface which faces the nerve fiber bundle when implanted. In addition, a second electrode assembly for acquiring the ECG signal representing the heart activity is disposed on the biocompatible substrate. The second electrode assembly does not have to be applied to the same support substrate surface of the support substrate as the existing first electrode assembly.

The implantable electrode assembly, that is at least the first and second electrode assembly, is electrically connected to an analysis and control unit or is configured so as to be connectable therewith, in which the locationally selectively acquired, neuronal electrical signals as well as the ECG signal can be analyzed in a time-resolved manner so that a neuronal time signal can be derived which is correlated to the blood pressure. The analysis and control unit, configured as a digital signal processor or microcontroller, can process signal data and also generate control signals.

A first comparator unit connected to the analysis and control unit acts to determine a characteristic relative time delay between the metrologically acquired ECG signal and the neuronal time signal correlated with the blood pressure.

Advantageously, the time difference between the R wave of the ECG time signal and a signal flank point along the steeply rising positive signal flank of the measured time signal correlated with the blood pressure wave is determined. The measured neuronal time signal correlated with the pulse wave or the blood pressure is characterized by a signal form which is dependent on the configuration of the first electrode assembly and is usually multiphase, to which a characteristic signal flank point can be assigned which acts to determine a time delay with respect to the temporally advanced ECG signal. The time delay determined between the ECG signal and the blood pressure wave or the pulse wave or the measured time signal correlated with the blood pressure wave also acts to precisely match the production of engineered stimulation signals to the natural neuronal electrical signals propagating along the baroreceptive nerve fibers.

Furthermore, the analysis and control unit determines a time window within which the neuronal time signals correlated to blood pressure is over a specific amplitude level, that is the time window corresponds to the pulse duration of a blood pressure wave. For the purposes of manipulating blood pressure, the aim is to apply an engineered electrical stimulation signal within it, with the aid of the time window determined with the aid of the analysis and control unit, to the at least one selected baroreceptive nerve fiber, so that the brain receives the electrical stimulation signal with a signal duration which matches the natural pulse wave duration and at a time at which the brain expects the normal, that is natural, blood pressure signals.

Furthermore, the analysis and control unit is electrically connected to a first function generator which generates, within the time window determined by the analysis and control unit which has a determined time delay with respect to the ECG signal, an electrical stimulation signal composed of a plurality of n individual pulses the phase and temporal amplitude profile of which are matched to the phase and temporal amplitude level of the recorded neuronal time signal correlated with the physiological parameter, preferably blood pressure. Advantageously, the electrical stimulation signal differs only in the temporally varying amplitude level which, in the case of a high blood pressure therapy, is selected to be larger or higher than that of the neuronal time signal correlated with the natural blood pressure. In this manner, the brain receives the information concerning a greatly increased blood pressure, to counter which appropriate natural organic regulation mechanisms are activated.

In order to transform and pass on the electrical stimulation signal composed of a plurality of n individual pulses in the form of a current signal, the first function generator and also the first electrode assembly of the implantable electrode assembly are directly or indirectly connected via a first signal-current converter which supplies the electrical stimulation signal for selective electrical stimulation of the at least one nerve fiber to the first electrode assembly.

With the exception of the implantable electrode assembly, the first electrode assembly of which comes into physical, that is electrical contact with the epineurium of the nerve fiber bundle, all of the remaining components of the implantable assembly, that is the analysis and control unit, the first comparator unit, the first function generator as well as the first signal-current converter are integrated into one implantable module, that is surrounded in a fluid-tight manner by a capsule formed from biocompatible material, wherein at least one electrical connection structure is provided for electrical contact of the components included in the implantable module with the implantable electrode assembly.

By means of the temporally coherent matching of the selective electrical stimulation with the transmission of natural, neuronal electrical signals along selected baroreceptive nerve fibers, as well as by matching the stimulation signals to the signal duration and signal form of the natural baroreceptive neuronal signals, the difference is only reflected in a temporally varying amplitude level which is usually raised, that is higher compared with the natural baroreceptive signals. Clearly, it is also possible to apply smaller amplitude levels to the at least one selected nerve fiber with the aid of the implantable assembly in accordance with the invention. In order to quantitatively establish the magnitude of the extra or reduced engineered amplitude, the implantable assembly provides at least one second comparator unit which is electrically connected to the analysis and control unit, which compares at least one signal level which is associated with the neuronal time signal correlated with the blood pressure with at least one reference signal and as a result generates a differential level value. The analysis and control unit also establishes, at least on the basis of the determined differential level value, at least the temporal amplitude profile of the stimulation signal, that is if the neuronal time signal correlated with the blood pressure measured with the aid of the implantable assembly differs significantly from the predetermined reference signal then, depending on the regulation requirement, the temporally varying amplitude level of the electrical stimulation signal is raised or reduced with respect to the measured time neuronal time signal correlated with the blood pressure. In the event of a high blood pressure therapy, it is usually necessary to raise the temporally varying amplitude level significantly in order in this manner to supply the brain with information regarding an elevated blood pressure which then, in the context of natural organic or biological regulation mechanisms, will seek to reduce the detected excessive blood pressure level.

The electrical stimulation explained above, which is illustrated with the aid of the cuff electrode assembly shown in FIGS. 2a and 2b, is carried out along the baroreceptive nerve fibers with isotropic signal coupling, that is without setting a fixed signal propagation direction, so that the electrical stimulation signals can propagate both along afferent and along efferent nerve fibers. In order to prevent electrical stimulation signals from being propagated along efferent nerve fibers, that is directed towards the heart, without thereby exerting a significant negative influence on non-baroreceptive, afferent as well as efferent nerve fibers within the nerve fiber bundle, a cuff electrode assembly which is modified compared with the electrode assembly described in FIG. 2 is appropriate, which is supplemented by at least one third electrode assembly for inhibiting a unidirectional electrical signal transmission along at least one selected nerve fiber within a nerve fiber bundle.

The third electrode assembly which is also positioned on the same support substrate formed as a single piece on the same support substrate surface as the first electrode assembly, is in a spatially fixed association with the first electrode assembly, in particular with the first electrode contacts of the at least three first electrode structures, with the aid of which baroreceptive nerve fibers within the nerve fiber bundle are locationally selectively acquired and, moreover, can be selectively electrically stimulated. When the localized baroreceptive nerve fibers are known, the third electrode assembly can be used for the purposes of a selective inhibition of the baroreceptive nerve fibers in order to suppress further transmission of electrical stimulation signals along efferent nerve fibers, that is leading to the heart. In this regard, there are at least two, preferably four or more second electrode contacts of at least one third electrode structure which, like the first electrode contacts of one of the at least three first electrode structures, are distributed uniformly in the circumferential direction of the support substrate surface orientated to face the nerve fiber bundle and forming a right cylinder. To inhibit localized efferent baroreceptive nerve fibers, at least one of the third electrode contacts of the third electrode structure is activated electrically, whereupon specific, temporally limited selective inhibition of the efferent nerve fiber in question is carried out. In this regard, an electrical polarization field enters the nerve fiber bundle from the respective at least one activated third electrode contact and interacts primarily with the nerve fiber to be inhibited. In order to axially limit the electrical polarization field propagated into the nerve fiber bundle during inhibition, each third electrode structure uses second electrode strips applied axially on both sides which, when the cuff electrode is implanted, constitute ring electrodes which completely surround the nerve fiber bundle.

For the purposes of inhibiting selected efferent nerve fibers, the modified implantable electrode assembly should be applied to the nerve fiber bundle in a manner such that the additional third electrode assembly is orientated towards the heart or the baroreceptive receptors, that is caudally, and the first electrode assembly which is concerned with the selective acquisition of neuronal electrical signals and also the electrical stimulation of localized nerve fibers, is orientated towards the brain, that is rostrally, along the nerve fiber bundle.

With the aid of the third electrode assembly, inhibition can be carried out either by means of what is known as an anodal block or by the application of sinusoidal signals with frequencies in the kilohertz range. In the case of anodal blocking, at least one of the second electrode contacts is polarized anodically, whereupon a prevailing voltage is produced at the location of the efferent nerve fiber through which an activating stimulation of the appropriate nerve fiber is suppressed. Similarly, inhibition can be obtained by applying a high frequency signal, wherein a high frequency electrical inhibition signal is applied to at least one selected third electrode contact, whereupon the electrical signal transmission mechanisms along the efferent nerve fibers come to a standstill for a brief period.

In both cases, despite being very close to the first electrode structure, because it is so narrow, given by the axial separation of both third electrode strips, the third electrode assembly provided in accordance with the invention is axially spatially limited along the efferent nerve fibers to be inhibited, although the implantable electrode assembly should not exceed an axial length of 4 cm, so that the first electrode assembly disposed on the brain side along the nerve fiber bundle can be coupled into the respective localized afferent nerve fibers guiding electrical stimulation signals to the brain without being influenced by the inhibition mechanism. In this manner, any side effects caused by possible direct stimulation in the direction of the nerve fibers leading to the heart, that is efferent nerve fibers, can be eliminated.

Advantageously, the third electrode contacts of the third electrode structure, when the cuff electrode has been implanted, are uniformly distributed along a virtual circle in order in this manner to selectively and effectively inhibit localized efferent nerve fibers relative to the circumferential edge of a nerve fiber bundle.

However, in an advantageous embodiment, it is not necessary for the third electrode contacts to be identical in form and size, wherein their axial extents are respectively selected so as to be identical, and the same is the case for the axial extents of the first electrode contacts of the first three electrode structures. The circumferential extent of the respective third electrode contacts is selected so as to be larger than the circumferential extent of the first electrode contacts. Thus, the third electrode contacts preferably have a larger surface area compared with the first electrode contacts, whereupon the locational selectivity, by means of which the third electrode contacts can electrically polarize specific efferent nerve fibers, is smaller than the locational selectivity with which the first electrode contacts can electrically stimulate localized nerve fibers. Alternatively, instead of a rectangular shape, the third electrode contacts may also be configured as circular contacts. This has the advantage that no voltage field peaks are formed that are caused by edges or corners.

The third electrode assembly is preferably configured in the form of a tripolar electrode assembly, that is, the third electrode structure is axially bordered on both sides by a third electrode strip each configured as a ring, wherein the axial distance between two third electrode strips along the support substrate is preferably selected so as to be between 0.5 cm and 3 cm, in particular between 0.75 cm and 1.25 cm. The circular third electrode strips preferably have an axial extent in the range 1 µm to 5 mm, preferably in the range 100 µm to 4000 µm.

The third electrode contacts of the third electrode structure are disposed axially centrally between both third electrode strips and have an axial extent such that the respective axial distance to the second electrode strips is larger than their actual axial extent.

Particularly having regard to the possibility of carrying out depolarizing measures, instead of a third electrode structure, it is possible to envisage disposing three axially separated third electrode structures between the third electrode strips simultaneously with configuring the respective first electrode structure within the first electrode assembly. For completeness alone, it should be mentioned that it would also be possible to envisage even more than three first and third electrode structures between the respective first and third electrode strips. Thus, three, five, seven or more odd numbers of first and/or third electrode structures could be provided.

In a preferred exemplary embodiment, a third electrode structure comprises four third electrode contacts the electrode contact area of which is respectively less than one quarter of the contact area of a respective third electrode strip. Since the first or third electrode strips provided in both the first and also in the third electrode assembly each act as a ground or counterpole for polarization of the respective first or third electrode structure, because of charge symmetry considerations, the surface areas of the first and third electrode strips are each selected so as to be identical. However, an individual independent surface area selection may also be envisaged when configuring the first and third electrode strips.

Furthermore, it has been shown to be advantageous if all electrodes of the third electrode assembly, that is the third electrode contacts and third electrode strips, are produced from an electrically conductive material which has a lower charge transfer capacity than the electrode material from which the first electrode contacts of the first electrode assembly are formed. A particularly suitable material with a particularly high charge transfer capacity has been shown to be iridium oxide for the production of the respective first electrode contacts of the first electrode assembly, whereas the material for the third electrode contacts and third electrode strips consists of platinum or an electrically conductive polymer.

All of the electrode contacts of both the first and also third electrode assembly are preferably flush with the support substrate surface of the support substrate or set back with respect to thereto, so that they do not protrude beyond the support substrate surface, in order to provide as innocuous a surface contact as possible with the epineurium of the nerve fiber bundle. Because of the non-invasive surface contact, the implantable electrode assembly can easily be applied along the nerve fiber bundle and positioned, whereby the epineurium is not irritated at all or is only irritated to a minimal extent.

In order to combat further implantation-related tissue irritation and inflammatory reactions, at least one of those regions of the support substrate having a biocompatible polymer which comes into direct surface contact with the nerve fiber bundle may be provided with an inflammation reaction-inhibiting substance. A furtherway for reducing mechanical irritation to the nerve fiber bundle which could arise due to surface contact with the cuff electrode relates to rounding axial marginal edges of the support substrate surrounding the nerve fiber bundle in a manner such that in the region of the right cylindrical support substrate surface orientated towards the nerve fiber bundle, the biocompatible support substrate respectively has opposing edge regions where the support substrate has a greater substrate thickness than in the remaining support substrate region, wherein the edge regions have rounded marginal edges.

In the region of the third electrode assembly which acts to carry out electrical inhibition of localized nerve fibers, in a further preferred embodiment, at least one and preferably a plurality of optical waveguide openings or apertures are provided through which light can be applied or coupled through the epineurium of the nerve fiber bundle. The optical waveguide openings are preferably disposed axially adjacent to both second electrode strips and match the form, size and distribution of the third electrode contacts of the third electrode structure. By providing a plurality of spatially separated optical waveguides which lead to the support substrate surface facing the nerve fiber bundle, coherent or different optical signals with different wavelengths can be applied to the nerve fiber bundle for the purposes of optically activating optogenetic neuronal reactions within the nerve fiber bundle. In this manner, by means of a plurality of suitably disposed optical waveguide openings or apertures within the nerve fiber bundle, neuronal activation or inhibition reactions can be locationally selectively triggered as an alternative to or as a complement to the neuronal processes caused by the electrode contacts can be undertaken.

As already mentioned, the implantable electrode assembly in accordance with the invention is applied along the nerve fiber bundle in a manner such that the third electrode assembly lies along the nerve fiber bundle in the direction towards the heart. This ensures that efferent nerve fibers can be inhibited, whereas the first electrode assembly orientated towards the brain along the nerve fiber bundle can be used for the purposes of selective stimulation of localized afferent nerve fibers, that is nerve fibers which lead to the brain. If it is necessary to inhibit afferent nerve fibers selectively, then the modified implantable electrode assembly may be implanted along the nerve fiber bundle in the opposite orientation. In a further possible embodiment, a second inhibiting third electrode assembly is provided which is provided axially adjacent to the first electrode assembly opposite the third electrode assembly.

Intracorporeal implantation of the electrode assembly surrounding the nerve fiber bundle in a cuff is also confronted with the fundamental problem that the electrode strips and electrode contacts applied to the polyimide support substrate are constantly exposed to a moist medium, whereupon degradation may occur, in particular at the flat connections between the electrode contacts and the polyimide support substrate, which leads to local detachment and, associated therewith, at least to contact degradation via which, finally, the efficiency of the electrode assembly is compromised. In order to combat these detachment occurrences between metallic electrode contacts and the polyimide support substrate, in a preferred embodiment, at least the first and third electrode strips are each provided with at least one local opening, wherein the surfaces of the first and third electrode strips are connected to the support substrate or the support substrate surface so that the constituent polymer or polyimide of the support substrate at least partially penetrates through the at least one opening. In this manner, improved mechanical anchoring of the respective electrode strips with the support substrate is obtained.

A further possibility for an enduringly stable connection between the electrode contacts or electrode strips and the biocompatible polyimide or polymer material of the support substrate is reflected in a special configuration of the electrode contacts or electrode strips and in a specific integration of the electrodes into the support substrate. In this regard, the first and third electrode strips in particular each have a metallic base plate with a flat upper and lower side with at least one, preferably a plurality of structural elements locally protruding orthogonally from the upper side of the base plate, which are preferably configured as columns, ribs, sleeves or webs. The metallic base plate is completely surrounded by the biocompatible polymer of the support substrate with the exception of a first surface region of the at least one structural element which is orientated facing the support substrate surface and which does not protrude over it. This reduces the freely accessible electrode contact surface area on the support substrate surface, but because of the hermetic encapsulation of the base plate and also the one piece structural elements associated therewith, with the exception of the surface regions orientated to face the support substrate surface, it is completely surrounded by the biocompatible polymer of the support substrate. Ingress of liquid medium or moisture associated with the medium between the electrode strips and the biocompatible polymer of the support substrate is made substantially more difficult, so that degradation events can be largely excluded. In a further preferred embodiment, preferably between the lower side of the metallic base plate and the biocompatible polymer of the support substrate a layer of bonding agent or an assembly of layers of bonding agent is inserted, which combats possible moisture-related detachment incidents.

The implantable assembly in accordance with the invention advantageously enables a method for locationally selective acquisition of neuronal electrical signals which propagate along at least one nerve fiber contained in a nerve fiber bundle of a human or animal organism, as well as for selective electrical stimulation of the at least one nerve fiber, to be carried out. Particularly in the case of the electrical stimulation of afferent nerve fibers, that is nerve fibers along which neuronal electrical signals are guided to the brain, the electrical stimulation in accordance with the invention causes no or no significant irritation of the brain function because it is not possible to make a distinction in the brain between natural neuronal electrical signals and electrical stimulation signals. The method in accordance with the invention is characterized by the following steps of the method:

Firstly, neuronal electrical signals propagating along a nerve fiber which are to be manipulated are locationally selectively acquired. This step may be carried out with an electrode assembly which is known per se. On the basis of the acquired natural neuronal electrical signals, "artificial" electrical signals are generated having a signal duration and temporal amplitude corresponding to the acquired natural neuronal electrical signals. Depending on the therapeutic goal, for example reducing or raising the blood pressure, the "artificially" generated electrical signals are modified in a manner such that the amplitude of the electrical signal is raised or reduced at least within a temporal part section of the signal duration. Preferably, the temporal amplitude profile of the electrical signal is coherently raised or reduced in its entirety, that is over the entire signal duration of the electrical signal. In this manner, electrical stimulation signals are obtained which are applied to the nerve fiber in temporal phase with the neuronal electrical signals. This means that the natural neuronal electrical signals are temporally coherent, that is their temporal signal duration and temporal sequence along the nerve fiber can be overwritten by an electrical stimulation signal. This temporally coherent overwriting procedure means that the information within the natural neuronal electrical signal is replaced by artificially produced information impressed with the electrical stimulation signal.

Because the electrical stimulation signals propagate along the afferent nerve fibers in the same temporal sequence and with the same temporal signal duration as the original neuronal signals, it is not possible to differentiate the neuronal electric signals from the electrical stimulation signals in the brain.

In order to prevent electrical stimulation signals applied to the respective nerve fiber from propagating bidirectionally along the nerve fiber, in a preferred development, temporally prior to and/or during application of a respective electrical stimulation signal to the nerve fiber, an electrical inhibition signal is applied to the nerve fiber in a manner such that the electrical stimulation signal can only propagate unidirectionally along the nerve fiber. Suppression of signal propagation in the unwanted nerve fiber direction is preferably carried out with the aid of an additional electrode assembly which is separate from the electrode assembly acting to apply the electrode stimulation signals, which is positioned in the vicinity of the location at which the electrical stimulation signal is applied along the nerve fiber and in the opposite direction to the direction of propagation of the electrical stimulation signal.

All other advantageous features of the implantable assembly will be illustrated below with reference to the figures.

BRIEF DESCRIPTION OF THE DRAWINGS

The invention will now be described without limitation to the general inventive concept and with the aid of exemplary embodiments made with reference to the drawings, in which:

FIG. 5 shows an illustration of two alternative operational modes for the implantable assembly for blood pressure regulation;

FIG. 7a shows an illustration of an electrode strip with an opening;

FIG. 7b shows a detailed representation of an electrode strip integrated into the support substrate; and FIG. 7c shows an alternative configuration of a structural element;

DETAILED DESCRIPTION OF THE INVENTION

Figure 1:
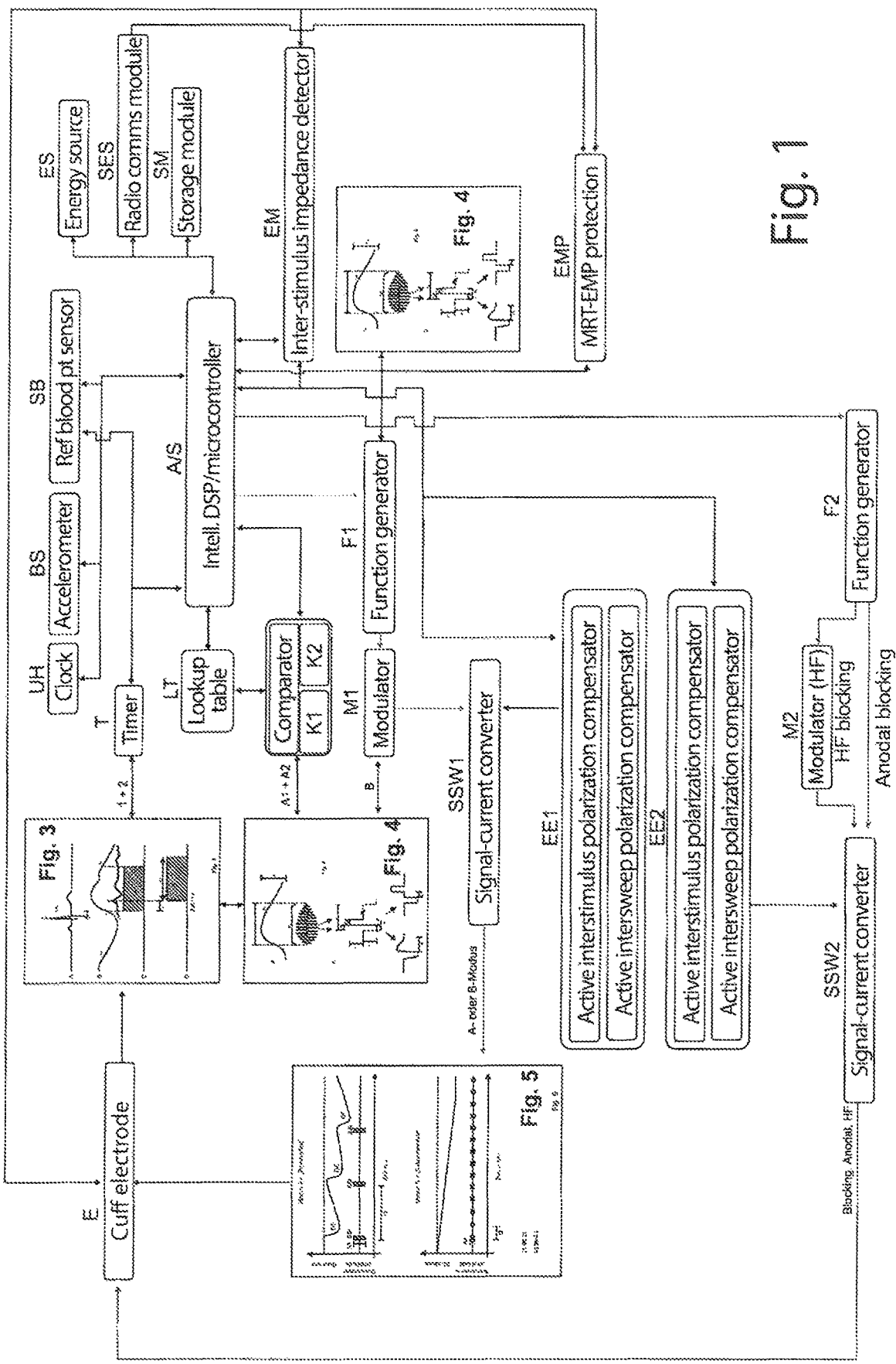
FIG. 1 shows a block diagram of all of the components of the implantable assembly in accordance with the invention.

FIG. 1 shows a block diagram which illustrates the individual components of the implantable assembly which respectively are interconnected via primarily bidirectional electrical communication pathways as shown with connecting arrows. The individual communication pathways may be in the form of wired or wireless connecting lines via which the electrical signals for informal data transfer as well as electrical energy transfer can be transmitted bidirectionally.

The main components of the implantable assembly are the implantable electrode assembly E, the analysis and control unit A/S, a first comparator unit K1 electrically connected to the analysis and control unit A/S, a first function generator F1 also connected to the analysis and control unit A/S, as well as a first signal-current converter SSW1 connected to both the first function generator F1 directly or indirectly as well as to the implantable electrode assembly E.

In a first embodiment, the implantable electrode assembly E corresponds to an electrode assembly which is known per se, as illustrated in FIGS. 2a and 2b, which can be applied around a nerve fiber bundle in a cuff, wherein for the purposes of selective detection of electrical neuronal time signals, first electrode structures 3 configured as tripole assemblies are preferably provided, which are respectively axially bordered on both sides by first electrode strips 5 which are in the form of rings when implanted as shown in FIGS. 2a and 2b, in this regard.

In addition, the implantable electrode assembly E is provided with at least one electrode for acquisition of the ECG signal. As an example, it is possible for an ECG signal of this type to be picked up with the aid of the reference electrode 12 in the implantable electrode assembly illustrated in FIG. 2a.

Figure 3:
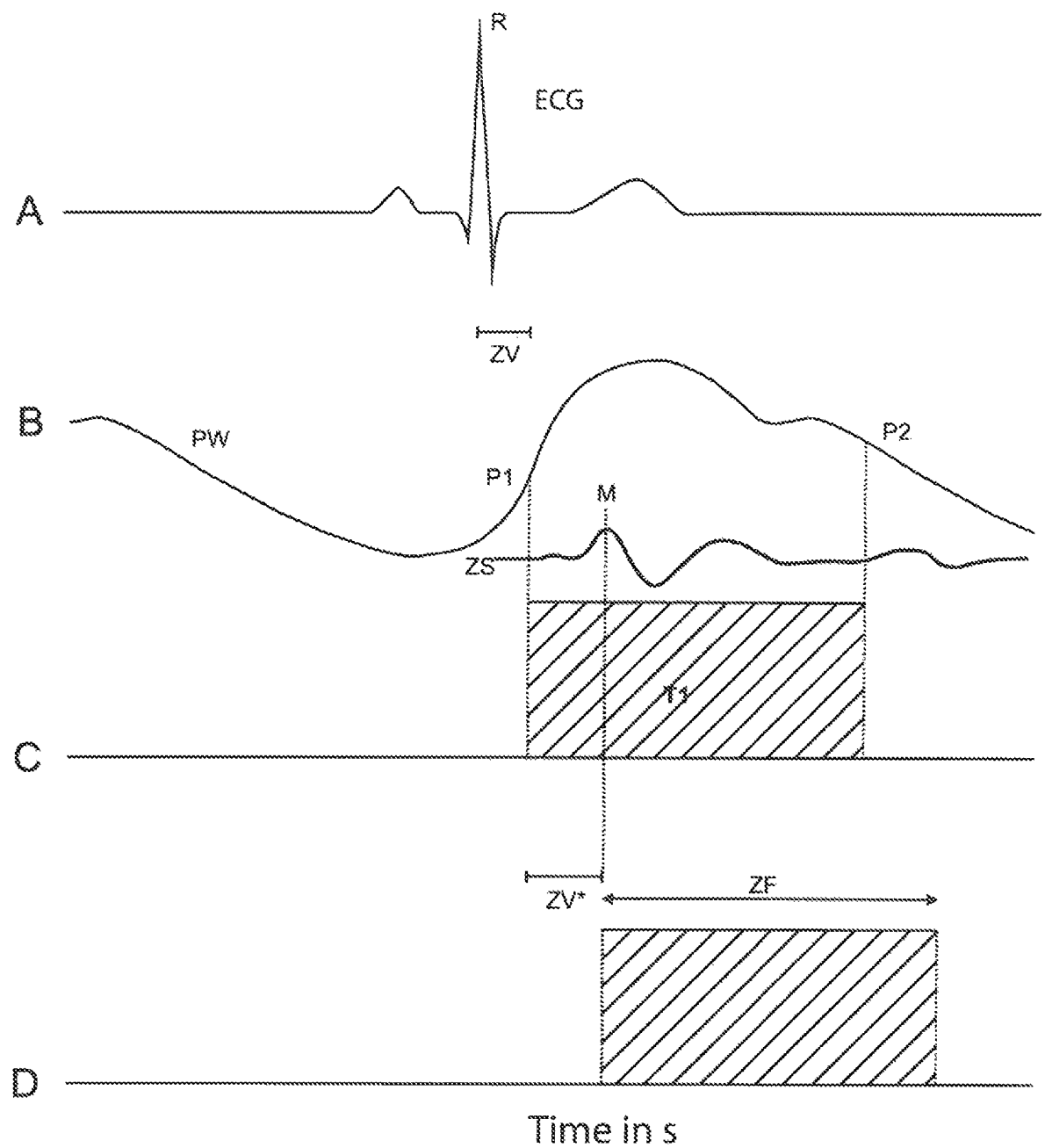
FIG. 3 shows time diagrams to illustrate the ECG signal and the neuronal time signal correlated with the blood pressure.

The electrical information detected with the aid of the electrode assembly E, both the ECG signal as well as the neuronal electrical time signal correlated with the blood pressure, are supplied to the analysis and control unit A/S in a time-resolved manner for further analysis. Preferably, a timer unit T is used for the time-resolved acquisition and transfer of the electrical signals to the analysis and control unit A/S. FIG. 3 provides a better understanding of the function of the implantable assembly. It shows the temporal relationships between an ECG signal acquired with the aid of the second electrode assembly applied around the vagus nerve in the region of the carotid artery. See wave form A. The natural pulse wave or blood pressure wave PW through the aorta is shown as wave form B which, for example, can be acquired with a dedicated blood pressure sensor within the aorta in the immediate vicinity of the heart, as well as a neuronal time signal ZS shown as wave form C which is correlated with the blood pressure and derived from the neuronal electrical signal.

The baroreceptors in the wall of the aorta are stimulated by the mechanical pulse wave PW, whereupon the baroreceptors transmit frequency-encoded neuronal electrical signals which depend on the strength of the pulse wave PW. This synchronous stimulation of several hundred baroreceptors in total produces the neuronal electrical signal which can be picked up via the cuff electrode applied around the vagus nerve.

To technologically stimulate the vagus nerve for the purposes of overwriting natural neuronal electrical signals which are directed along the vagus nerve for the purposes of therapy, at least two time delay effects have to be taken into account which have to be considered or compensated for when carrying out the engineered stimulation in order to make the stimulation appear as natural as possible in order to prevent the brain from subsequently being irritated by the engineered signal.

On the one hand, this concerns the time delay ZV between the start of the ECG signal, or the R wave, of the ECG signal, as shown as FIG. 3A. The rise of the blood pressure wave PW in the aorta, is at point P1 in FIG. 3B. On the other hand, this concerns the time delay ZV* between stimulation and transduction of the baroreceptors and the neuronal electrical time signal ZS until it has reached the region at which the cuff electrode E should overwrite the natural blood pressure signal. This time delay ZV* is typically selected to be between the point P1 and a first maximum M of the neuronal electrical time signal ZS.

The neuronal electrical time signals ZS may appear different, but usually they have a "sombrero" shape and thus have several "vibrations". It might initially appear to be odd that the pulse wave signal PW from the baroreceptors is not encoded as a "wave form". The reason for this is because of the tripolar configuration of the first electrode assembly. Thus, the "single peaked" natural neuronal electrode pulse wave signal runs along the vagus nerve in the longitudinal direction past the three electrode structures of the first electrode assembly and can polarize them temporally one after the other. In this manner, the monophase neuronal electrical signal is converted into the multiphase neuronal electrical time signal ZS.

The derived multiphase neuronal electrical time signal ZS also always sits temporally between a characteristic flank rise point P1 and a flank fall point P2 of the pulse wave PW. That is within the time window T1 which corresponds to the temporal duration of the pulse wave PW.

Considering the time delays ZV and ZV* discussed above, the electrical stimulation signal has to be generated within the time window ZF. See FIG. 3D. The electrical signal can be applied via the first electrode assembly to the vagus nerve for the purposes of a selective stimulation of the at least one baroreceptive nerve fiber.

In contrast to the acquisition and metrological use of the ECG signal, determining the neuronal electrical time signal ZS correlated with the blood pressure as shown in FIG. 3C, requires special signal processing or signal preparation, especially if the signal level of the measured time signal ZS correlated with the blood pressure cannot be distinguished from the surrounding electrical noise level. In this regard, with the aid of the neuronal electrical signals obtained from the implantable electrode assembly, preferably, coherent averaging, preferably with the ECG signal as a trigger, is undertaken, wherein all of the parts of the signal undergo additional amplification which reproducibly follow the blood pressure. Further details in this regard can be obtained from the contribution cited above by Dennis T T Plachta, Oscar Cota, Thomas Stieglitz, Mortimer Gierthmuehlen, "Selektive Ableitung und Stimulation für ein blutdrucksenkendes Implantat unter Verwendung von Vielkanal-Cuff-Elektroden" [Selective Recording and Stimulation for a Blood Pressure-Reducing Implant Using Multi-Channel Cuff Electrodes], tm—Technisches Messen, 2013, vol 80 (5), pp 163-172.

With the aid of the neuronal electrical time signal ZS correlated with the blood pressure, which is shown in FIG. 3C, with its temporally varying amplitude profile, the time delay ZV to the ECG signal can be determined as shown in FIG. 3A. At this point, it should be noted that the neuronal electrical time signal ZS correlated to the blood pressure, which can be determined with the implantable assembly, only corresponds to a relative blood pressure value, that is the electrical potentials rise and fall along with the blood pressure. The time signal maximum does not constitute an absolute blood pressure in mm Hg. Absolute blood pressure determination thus requires an additional external or internal reference sensor to be provided, with which the absolute blood pressure can be acquired. For the purposes of calibration of the time signal ZS obtained with the implantable electrode assembly, preferably, a technical blood pressure sensor which is also implantable is used, for example a tip catheter, which is known per se, or an extracorporeally positionable blood pressure cuff. In this regard, FIG. 1 shows the reference blood pressure sensor SB as a further component which does not necessarily have to be configured as an implantable unit. Preferably, the absolute blood pressure determined with the aid of the reference blood pressure sensor SB is also fed to the analysis and control unit A/S in a time-resolved manner. The time is recorded by a clock UH which exchanges data with the reference blood pressure sensor SB.

In order to stimulate the baroreceptive nerve fibers electrically within the nerve fiber bundle surrounded by the implantable electrode assembly E in a cuff which is required for effective blood pressure therapy, an analysis of the ECG signal as well as the neuronal electrical time signal correlated with the blood pressure is required. The analysis in this regard takes place in the analysis and control unit A/S, with the aim of determining exactly that point in time at which the brain expects the baroreceptive signals transmitted via the baroreceptive nerve fibers. The technical electrical stimulation of the nerve fibers transmitting the blood pressure signals should also match with the natural blood pressure signal delivery regarding timing, temporal duration and the qualitatively temporally changing signal form. The ECG signal is acquired in a monopolar manner as an artefact of the timer or trigger signal, for example, via the reference electrodes 12 as shown in FIG. 2A. The ECG signal is transmitted to the analysis and control unit A/S as the time signal. Next, the time delay ZV between the ECG and the natural pulse wave PW is determined in the analysis and control unit A/S. In this regard, in particular, the time difference between the R wave of the ECG signal and a characteristic signal flank point P1 along the rising starting flank of the blood pressure wave PW is used. The time delay ZV in a person with a normal pulse (65 bpm) will be <200 ms See the time axis in seconds in FIG. 3A. Furthermore, in the context of the analysis and control unit A/S, the characteristic pulse duration T1 of the pulse wave PW is measured, which is given by the temporal separation between the first signal flank point P1 and a second signal flank point P2 along the falling signal flank.

Furthermore, within the analysis and control unit A/S and taking biologically conditioned delays into consideration, for example time delays conditioned by transduction of a mechanical event (pulse wave) into a bioelectrical signal and/or by conversion of an engineered current signal into a bioelectrical neuronal potential and/or by the time delays brought about by the characteristic line velocities along neuronal fibers, a corrected time delay ZV* is determined which is taken into consideration when generating a stimulation signal.

Thus, the at least one baroreceptive nerve fiber is electrically stimulated within a specific time window ZF which lies in a defined time delay ZV+ZV* with respect to the acquired ECG signal. This is carried out with the aid of the function generator F1, which generates a stimulation signal SSI composed of a plurality of n individual pulses and which matches the neuronal electrical signal SN correlated with the natural blood pressure, as shown in FIG. 4A, in phase and temporal amplitude. In this regard, it should be noted that the natural neuronal electrical signals SN propagated along baroreceptive nerve fibers are identical to the form and pulse duration of a blood pressure or pulse wave PW having regard to the temporal duration TSN and amplitude profile.

The function generator F1 then modulates the amplitudes of the n individual pulses EP. In FIG. 4A the stimulation signal SSI is composed of 13 individual pulses but in reality, 100 to 200 individual pulses produce a stimulation signal and thus approximates to the biological pressure profile in the stimulation signal SSI acquired with the implantable electrode assembly E as an envelope function. In order to establish the temporally variable amplitude profile of the stimulation signal SSI, that is the matched amplitudes of the individual pulses EP within a stimulation signal, the pulse duration T1 of the time signal sz correlated with the blood pressure as well as its maximum amplitude Amax are employed. Advantageously, the pulse duration T1 as well as the maximum amplitude Amax are determined within the first comparator unit K1.

Figure 2:
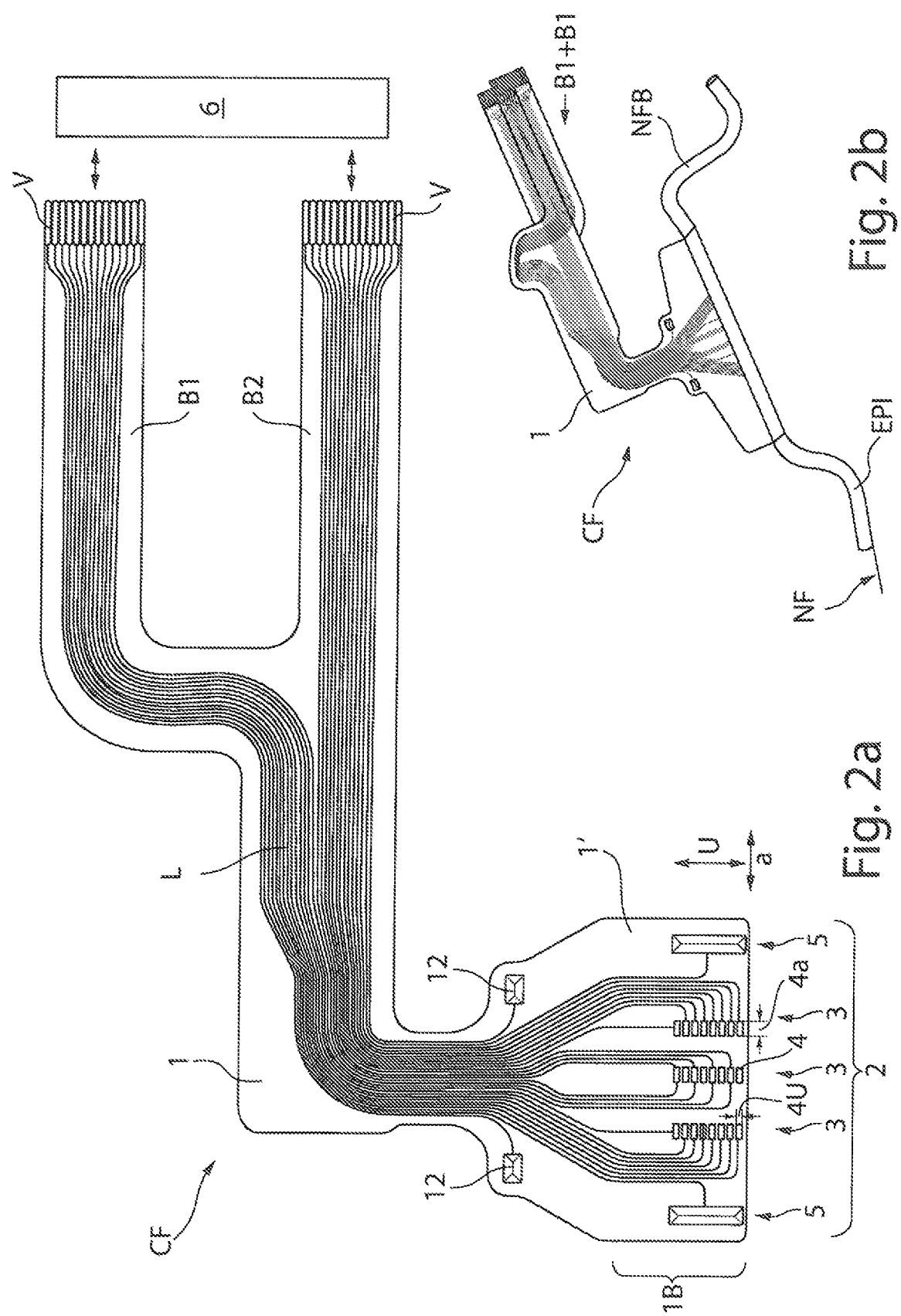
FIGS. 2a and 2b show an implantable electrode assembly in accordance with the prior art.

Each individual pulse EP has characteristic parameters which are shown in FIG. 4B. Thus, each individual pulse EP has a cathodic signal portion KT and an anodic signal portion AT. The anodic signal portion AT of each individual pulse EP has an anodic amplitude in amperes, E1, as well as an anordic pulse width E4. Similarly, the cathodic signal portion KT has a cathodic amplitude in amperes, E2, and a cathodic pulse width E3. The repetition rate E5 is measured in Hz. The repetition rate E5 does not have to have a fixed frequency. It has been shown that neuronal systems neuronal nerve fibers, can best be stimulated if external electrical activation follows or corresponds to the natural typical pattern of neuronal activity, that is with a distribution function which preferably is a Poisson distribution. Production of the stimulation signal SSI composed of a plurality of n individual pulses EP is preferably carried out with the first function generator F1 in a manner such that the two phases of each individual pulse EP, that is the surface areas of the anodic signal portion AT and the cathodic signal portion KT are identical. Otherwise the electrode contacts, that is at least the electrode contacts 4 of the tripolar electrode structures 3, as shown in FIG. 2, would become charged, whereupon subsequent electrical stimulations would be applied to the at least one selected nerve fiber within the nerve fiber bundle with a significantly smaller efficiency. Furthermore, lack of charge balance can lead to corrosion by means of redox reactions if a DC voltage is built up by the polarization which exceeds the water window boundaries. The individual anodic and cathodic signal portions AT, KT of each individual pulse EP are produced by the first function generator F1 in the form of square wave signals.

Figure 4:
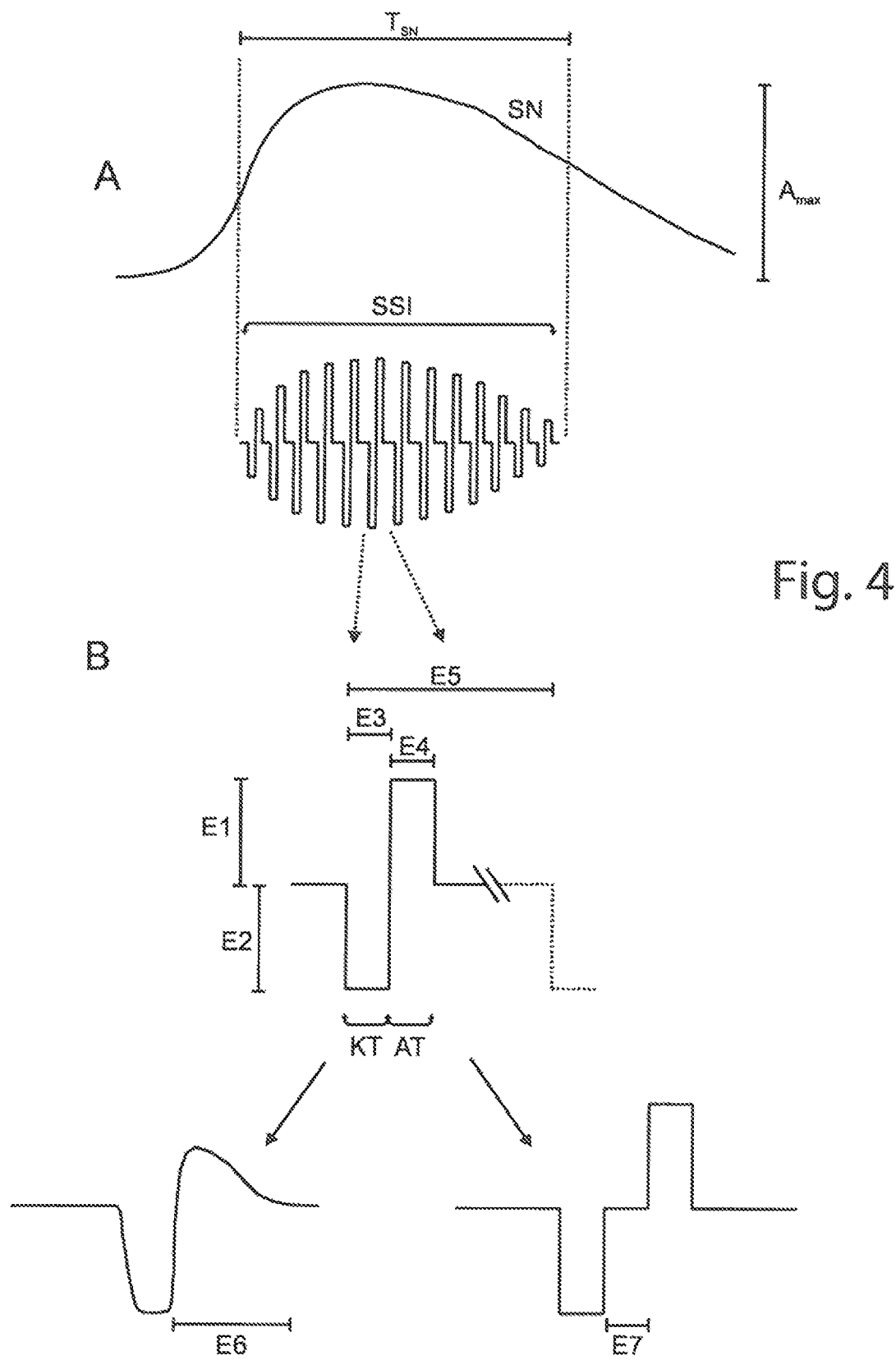
FIG. 4 shows an illustration explaining the stimulation signal composed of n individual pulses as well as explaining an individual pulse.

It has also been shown to be advantageous when the signal flanks of each individual pulse EP are advantageously "rounded off" to a certain extent in order to reduce the corrosion effects arising at the metal contacts of the individual electrodes of the implantable electrode assembly, service life can be improved. An engineered signal flank rounding of this type, in particular of the repolarization flank E6, shown at the bottom left of the of FIG. 4B, along with the improved electrochemical properties discussed above proves to be even better with regard to the biological effectiveness during electrical stimulation of the at least one selected nerve fiber. In this regard, a first modulator M1 is connected immediately downstream of the first function generator F1 seen in FIG. 1. The modulator M1 can primarily take the rectangular repolarizing signal portion AT and temporally extend or smooth it compared with the polarizing signal portion KT. As a result, both signal portions AT and KT have coherent, that is identical signal strengths, in order to allow complete repolarization of the electrode contacts. Alternatively or in combination with the above measures for rounding at least the repolarizing signal portion AT, a further advantageous influence that the first modulator M1 has on each of the individual pulses EP generated by the first function generator F1 is the temporal decoupling between the cathodic signal portion KT and the anodic signal portion AT by a temporal break E7 as shown in FIG. 4, bottom right hand side. As a result, an extremely long signal flank between the cathodic and anodic signal portions KT and AT is avoided, whereupon unwanted neurostimulating artefacts can be excluded. Clearly it is also possible to modulate the temporal duration of the break E7.

All of the individual pulse characteristics E1 to E7 described above and shown in FIG. 4 can be individually set up and adjusted by the first modulator M1.

The implantable assembly can autonomously decide, as a function of individual regulation requirements for the purposes of levelling the blood pressure, as to whether, when and to what strength and duration electrical stimulation signals SSI should be applied to the at least one baroreceptive nerve fiber. In this regard, the implantable assembly in accordance with FIG. 1 is provided with at least one second comparator assembly K2 which is electrically connected to the analysis and control unit A/S. The second comparator assembly K2, which may be housed in the same unit as the first comparator unit K1, compares at least one characteristic signal level of the neuronal time signal ZS correlated with the blood pressure with a reference signal which is preferably stored in a Lookup table LT, which is connected to both the analysis and control unit A/S and the comparator unit K2, which generates a characteristic difference level on a basis of what the analysis and control unit A/S establishes at least as the temporal amplitude profile, with the temporally variable amplitude of the stimulation signal SSI. Finally, advantageously on the basis of at least the generated differential level value, all of the stimulation parameters E1 to E7 can be varied and coordinated so that all individual pulse forms can be individually selected in order to compose a stimulation signal SSI to be applied to the at least one baroreceptive nerve fiber.

Clearly, in addition to the reference signal stored in the Lookup table LT, further information characterizing the physiological condition of the respective patient may be stored for the purposes of electrical stimulation of the at least one baroreceptive fiber, such as, for example, information which characterizes the mobility status of the patient, the differential level value, acquired absolute blood pressure, etc.

Thus, in an advantageous embodiment the implantable assembly is provided with an accelerometer BS which is preferably integrated into the implantable module, in which the analysis and control unit A/S, the first and second comparator unit K1 and K2, the first function generator F1 as well as the first signal-current converter SSW1 are housed. The accelerometer BS is electrically connected to the analysis and control unit A/S and thus can supply the generated acceleration information to the analysis and control unit A/S for further analysis. It is also possible to use an extracorporal accelerometer positioned on the patient which provides acceleration information which can be communicated to the analysis and control unit A/S wirelessly, for example by inductive data coupling. The at least one and preferably triaxial accelerometer or movement sensor BS can record the physical activity of the respective patient, so that blood pressure rises conditioned by movement can be taken into consideration and recognized as such by the implantable assembly so that it does not lead to a blood pressure reducing stimulation of the at least one baroreceptive nerve fiber.

In addition to possibly producing and positioning a triaxial accelerometer or movement sensor outside the body, further extracorporal units may advantageously be provided such as, for example, an energy source ES, a storage module SM as well as a signal and energy supply unit SES. In order to transmit all electrical signals, and also to transmit electrical energy, wireless induction-based signal and energy transmission technology is used.

All information which is fed to the analysis and control unit A/S, in particular the intracorporeally acquired neuronal time signals ZS correlated to blood pressure as well as all extracorporeally provided information can be stored in the Lookup table LT and updated appropriately, so that the regulation mechanism at the basis of the implantable assembly can constantly refer to up-to-date information. As an example, in this manner, the neuronal time signals ZS correlated with the blood pressure picked up with the aid of the electrode assembly E, which only represents relative blood pressure signals, can be calibrated with up-to-date, absolute blood pressure values which can be acquired with the aid of the intracorporeal or extracorporal blood pressure measurement system SB. Furthermore, the implantable assembly configured in accordance with the invention enables self-regulating monitoring of the stimulation signals applied to the at least one baroreceptive nerve fiber wherein, with the aid of the electrode assembly E, organic feedback of the stimulations which occur can be recorded so that what is known as a closed loop regulation function can be obtained. Alternatively to or in combination with the lookup table mentioned above, a further storage zone may also be provided to hold information or signals, so that signals themselves can be stored when, for example, a state estimator and Kalman filter is used for regulation and lagging signals can affect the manipulated variable for the adjustments.

Referring now to FIG. 5, two different blood pressure regulation modes will now be discussed with which the implantable assembly can be used to affect the blood pressure. In both diagrams shown in FIG. 5, the respective top graph shows the blood pressure along the time axis t. The respective bottom graph in both diagrams shows the stimulation amplitude for a respective stimulation signal SSI in diagrammatic manner. In the case of the blood pressure regulation illustrated in the top of FIG. 5, it can be seen that immediately after activation and application of a stimulation signal SSI which has a stimulation amplitude A3, a dip DE, which significantly reduces the blood pressure is triggered. If the stimulation signal SSI is repeated at a repetition rate t1, then this results in a rapid drop in blood pressure until a desired blood pressure value is reached.

On the other hand, the blood pressure regulation mode B illustrated in the lower diagram results in a different response to natural physiological blood pressure regulation. In this case, then, the stimulation signals SSI are activated and applied with a much smaller stimulation amplitude A4 than in the case of the stimulation amplitude A3 in the regulation mode A described above, by use of a smaller stimulation signal amplitude A4 of this type, no acute dip DE is produced in the blood pressure value. Furthermore, if the temporal separation between the individual stimulation signals SSI are selected to be large enough in the case of regulation mode B (see time axis in minutes), that is very much longer than in the case of mode A, this leads to a very slow but steady drop in blood pressure, as can be seen from the blood pressure function in the case of regulation mode B. By means of regulation mode B, also termed a "secondary effect" in contrast to the "primary effect" which describes regulation mode A, a lot of energy can be saved when operating the implantable assembly. Furthermore, the load on the nerve tissue and also on the electrodes is substantially smaller, and in addition the blood pressure can be regulated carefully. Both the stimulation amplitude A4 and also the temporal repetition rate t2 can be selected individually in order to set a desired reduced blood pressure. The modus operandum described as regulation mode B is preferred for the therapy of chronic hypertension, whereas regulation mode A, described as the primary effect, may be of application in cases of hypertonic crisis.

The implantable assembly in accordance with the invention can automatically change between the two regulation modes during operation as a function of the occurrence of specific blood pressure situations, that is if blood pressure spikes are to be reduced as quickly as possible, then regulation mode A is suitable, but if on the other hand slow blood pressure corrections are preferred, then regulation mechanism B is used. In order to decide which of the two regulation mechanisms are to be applied, all of the updated recorded information in the lookup table as well as the information supplied to the analysis and control unit may be used.

As already discussed in connection with FIG. 4, the n individual pulses EP are composed of a cathodic and an anodic signal portions KT and AT, so that both polarization signal surfaces cancel each other out mutually (charge balanced stimulation), a residual polarization of the respective electrodes contributing to stimulation can be avoided. Despite these measures, it is possible that an admittedly small residual polarization (charge) on the electrodes cannot be excluded, with subsequent individual stimulation pulses affecting both pulse form and pulse strength. These unwanted effects caused by residual polarization have to be avoided.

To this end, in a further preferred embodiment of the implantable assembly in accordance with the invention, an electrode impedance measurement unit EM is provided. See FIG. 1. The unit EM, which forms part of the implantable module or is disposed on the support substrate 1, is electrically connected to the electrode assembly E as well as with the analysis and control unit A/S. The electrode impedance measurement unit EM is configured in a manner such that between each of the n individual pulses EP, an impedance measurement is made at least at the electrodes of the first electrode assembly and thus measures their polarization. The electrode impedance measurement unit EM is also connected to a first depolarization unit EE1 which is also a part of the implantable module or is positioned on the support substrate 1. In the event that a residual polarization is detected by the electrode impedance measurement unit EM, the first depolarization unit EE1 can depolarize individual electrodes by briefly activating the affected electrodes selectively by applying electrical signals. Furthermore, the first depolarization unit EE1 not only detects any residual polarization at the electrodes involved in stimulation between each individual pulse but also removes the residual polarization (charge) appropriately. Moreover the unit EZZ also carries out an appropriate polarization measurement and appropriate active depolarization after each individual stimulation signal SSI. As a result, all of the individual pulses EP can be produced free from or substantially free from polarization effects, so that each individual stimulation signal SSI is generated under identical electrical circumstances by the electrode assembly. In this manner, buildup of a DC voltage underlying the sequence of stimulation signals can be prevented.

Figure 6:
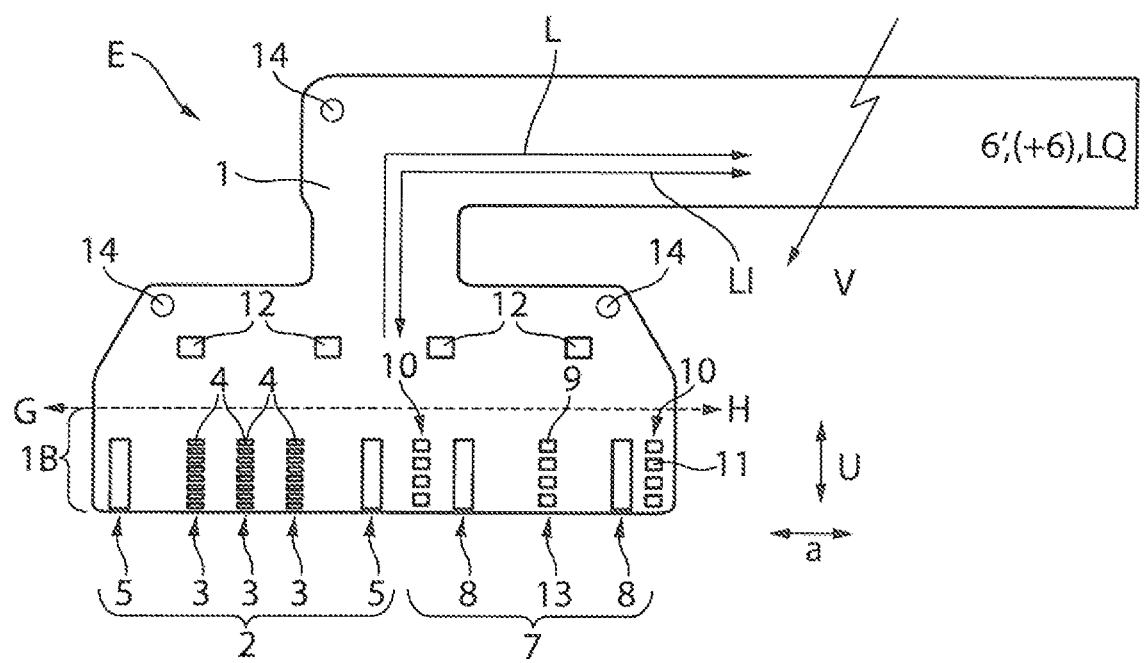
FIG. 6 shows a top view of a diagrammatic implantable electrode assembly with a third electrode assembly for selectively inhibiting nerve fibers.

In a preferred embodiment, the implantable assembly, configured in accordance with the invention, is provided with an electrode assembly E which is modified compared to the implantable electrode assembly E illustrated in FIGS. 2a and 2b, as illustrated in FIG. 6, which will be discussed further below, and which can actively suppress unwanted possible signal propagation along the baroreceptive nerve fiber in the direction of the heart, as can occur with the previously described electrode assembly.

To this end, the implantable electrode assembly is provided, on the right cylindrical support substrate surface facing the nerve fiber bundle when implanted, with a third electrode assembly 7 for inhibiting neuronal electrical signals propagating unidirectionally along the nerve fiber bundle. The third electrode assembly 7, which will be described in more detail below, is exclusively or primarily activated in connection with the electrical stimulation of the at least one baroreceptive nerve fiber. In this regard, a second function generator F2 is provided which is also integrated into the implantable module and generates an electrical signal known as a blocking or inhibition signal temporally before and/or during the determined time window t1, as shown in FIG. 4. The second function generator F2 as shown in FIG. 1 is also directly or indirectly connected to a second signal-current converter SSW2 which supplies the electrical inhibition signal to the third electrode assembly 7. In the same manner as the first function generator F1, the second function generator F2 is also capable of producing individual pulses which are each composed of a polarizing (charging) and a repolarizing (discharging) rectangular signal portion. In this case again, because of their polarity, both signal portions (charge) neutralize each other, so that after each individual pulse, almost no residual polarization (charge) remains at the respective electrode contacts 9.

Furthermore, a second moderator M2 is between the second function generator F2 and the second signal-current converter SSW2 which amplifies and smooths a signal flank profile associated with a discharging signal portion AT forming a rectangular pulse temporally with respect to the polarizing signal portion KT, harmonizes the signal strengths associated with the two signal portions. The measures connected to the second modulator M2 are taken for the same reasons as discussed above with respect to the first modulator M1. In addition to the second function generator F2, the second modulator M2 is also integrated into the implantable module. Again in the case of the second modulator M2, it is also optionally possible to temporally separate the polarizing signal portion for each individual pulse by a zero signal which can be produced in the second modulator M2 from repolarizing signal portions. In this manner, a long steeply falling signal flank between the two signal portions is avoided, which could lead to irritating inhibition effects or to additional stimulation of the nerve fibers under the outlying electrodes (what is known as rising break excitation).

Inhibition can be carried out with the third electrode assembly 7 either by way of what is known as anodal blocking or by the application of sinusoidal signals with frequencies in the kilohertz region, what is known as a HF blocking. In the case of an anodal block, at least one of the third electrode contacts is polarized anodically, whereupon a voltage is produced at the location of the efferent nerve fiber for suppressing stimulation of the corresponding nerve fiber. In this case, an additional modulation by the second modulator M2 is not required. Similarly, an inhibition with a high frequency signal application may be intended, wherein a high frequency electrical inhibition signal is applied to the at least one selected third electrode contact, whereupon the electric signal transmission mechanisms along the efferent nerve fibers briefly comes to a halt.

The third electrode assembly 7 for specific inhibition of stimulation signals propagating along the at least one selected baroreceptive nerve fiber unidirectionally, preferably in the direction of the heart, is similarly connected to the electrode impedance measurement unit EM, in order to record any residual polarization (charging) at the electrode contacts 8 and 9 of to the third electrode assembly. In order to appropriately depolarize any residual polarizations, again a second depolarization device EE2 is provided which can remove both residual polarizations between individual pulses and also between any sequential inhibition signals by metered electrical activation of individual electrodes.

For the purposes of electrical protection of the implantable assembly with respect to EMP protection as well as magnetic coupling by means of MRT, EMP unit is integrated into the implantable module. This unit monitors the inputs of the electrodes and enables decoupling in the event of externally evoked fluctuations in potential. In addition, the EMP unit is provided with a magnetic field sensor which, when a strong DC field is detected, activates a temporary self-protection program.

FIG. 6 shows a diagrammatic top view of a preferred implantable cuff electrode E on the support substrate 1 which is preferably produced from polyimide. A third electrode assembly 7 is provided, in addition to the first electrode assembly 2 for locationally selective detection of neuronal electrical signals and for the selective electrical stimulation of individual nerve fibers, for the inhibition of at least one selected nerve fiber. To avoid repetition, reference should be made to the discussions regarding the individual electrodes of the first electrode assembly 2 as well as the second electrode assembly 12 in the above description of FIGS. 2a and 2b.

The third electrode assembly 7 for inhibiting the signal propagation of efferent nerve fibers leading in this case to the heart H comprises two axially separated third electrode strips 8 between which a third electrode structure 13 is centered, and which has four separately disposed third electrode contacts 9. All of the electrodes 8 and 13 of the third electrode assembly 2 are positioned on the support substrate 1 or are connected to or are connectable to the analysis and control unit A/S via electrical conductors L. The electrical conductors L may optionally comprise a separable connecting structure V.

Optionally, the third electrode assembly 2 comprises optical waveguide assemblies 10 which each comprise four separate optical waveguide openings 11 distributed in the circumferential direction U. The optical waveguides LI run to the individual optical waveguide openings or apertures 11 within the support substrate 1 and can be combined proximally with a single light source LQ or with separate light sources LQ with different wavelengths of light, in order to selectively optogenetically activate stimulations and/or optically activate and selectively inhibit along specific nerve fibers.

Selection of the geometrical form and size of the individual electrodes, in the first and third electrode strips 5 and 8 as well as the first and third electrode contacts 4 and 9 can in principle be carried out individually with respect to each other and in particular comply with the diameter of the nerve fiber bundle around which the implantable cuff electrode E can be positioned. Thus, the extent in the circumferential direction U of the first and third electrode structures and electrode strips as well as, if appropriate, the optical waveguide assemblies 10 preferably correspond to the length of the circumferential edge of the nerve fiber bundle to be wrapped with the cuff electrode E. The axial separation of the tripolar electrode assembly should preferably be matched to the diameter and the resulting separation of what is known as the nodes of Ranvier in myelinized nerve fibers of the nerve fibers to be stimulated. In the embodiment shown in FIG. 6, the electrodes are shown as rectangular electrode contacts. Advantageously, in particular for the purposes of avoiding field line densification at the electrode rectangle edges, the electrode contacts are at least provided with rounded corners.

This is the case when inhibiting or activating large and myelinized fibers in man. It is only possible at locations along the nerve fiber where these fibers are not myelinized, that is at what is known as the nodes of Ranvier. With increasing diameter of the nerve fibers, the intervals, that is the axial distances between the nodes of Ranvier are larger, and so correspondingly, the axial distance between two axially separated first electrode strips 5 must be selected so as to be approximately the same length as the axial separation of the nodes or somewhat larger in order to reach the nodes of Ranvier of very large fibers with a sufficiently high statistical probability. The same is preferably also the case for the axial separation of the third electrode strips 8.

The total axial extent of the whole cuff electrode E should be matched to the intracorporeal sizes of the respective nerve fiber bundles, Typically, it should not exceed 4 cm.

The reference electrode contacts 12 applied at the rear of the support substrate 1 act to acquire the ECG signal and, if required, the intracorporeally detectable noise level.

In addition, the support substrate 1 is provided with at least one and preferably two or three openings 14 reinforced with metallic ring structures which serve to fasten the implanted electrode assembly CF onto the nerve fiber bundle. Fastening is carried out with a surgical suture which is threaded at least once through the openings 14 and is stitched into the tissue surrounding the nerve fiber bundle. In contrast to the region 1B of the support substrate which is rolled into a right cylinder on which the first and second electrode assemblies 2 and 7 are positioned so that they contact the surface of the epineurium of the nerve fiber bundle when implanted, the support substrate 1 adjacent to the support substrate region 1B sits as a flat surface to one side of the nerve fiber bundle and protrudes into the surrounding tissue. The metallic ring structures 14 should help in mechanically accommodating the fastening forces along the surgical suture and in preventing damage to the support substrate by incisions.

In order to roll the implantable electrode assembly E with a cuff around a nerve fiber bundle which is not shown in further detail, on the side H leading to the heart, the third electrode assembly 7 is disposed along the nerve fiber bundle. The first electrode assembly 2 for selective detection as well as selective stimulation of localized nerve fibers is positioned along the nerve fiber bundle on the brain side G.

Preferably, the first and third electrode strips 5 and 8 as well as the first and third electrode contacts 4 and 9 are evaporated or sputtered onto the support substrate. Galvanic reinforcement is possible. Laser structuring of thin metal films is also a possible technology. To join the first and third electrode strips 5 and 8 in particular to the support substrate 1 permanently, the electrode strips are provided with local openings 15 shown as FIG. 7a through which the polymeric material of the support substrate 1 passes or protrudes. The electrode contact 16 of each of the first and third electrode strips 5 and 8 are also flush with the upper side 1' of the support substrate and directly contact the surface of the nerve fiber bundle.

In order to improve the permanent connection of the electrode strips, a preferred embodiment integrates the electrode strips into the support substrate primarily in the following manner as shown as FIG. 7b.

With respect to FIG. 7b, the electrode strips 5 and 8 each have a metallic base plate 17 which has an upper side 18 and a lower side 19. In one piece with the upper side 18 of the base plate 17 and over the upper side 18, preferably distributed over the whole upper side, are orthogally projecting structural elements 20, preferably in the form of columns, ribs, webs or having sleeve-like protrusions which have a surface region 21 facing the support substrate surface 1' which can come into direct contact with the epineurium of the nerve fiber bundle. In addition, advantageously, a layer of bonding agent 22 is provided at least between the lower side 19 and the polymeric material of the support substrate 1 surrounding the base plate 17. The layer of bonding agent 22 can also be applied to the upper side 18. Particularly suitable layers of bonding agents of silicon carbide (SiC) as well as diamond-like carbon (DLC). Preferably, the electrode strips 5 and 8 are produced from iridium oxide, which counts among those materials with one of the highest charge transfer capacities.

A further improved variation for the construction of the structural elements 20 which are positioned in a distributed manner on the upper side of the base plate 17 is illustrated in FIG. 7c. FIG. 7c shows a longitudinal section through a structural element 20 which has an longitudinal extension LA orientated orthogonally to the upper side 18 of the metallic base plate 17 along which the structural element 20 is provided with at least a second surface region 23 which is orientated parallel to the upper side 18 of the metallic base plate 17 and onto which the layer of bonding agent 22 or an assembly of layers of bonding agent 22' is applied. The second surface region 23 is separated from the first surface region 18 and separately is completely surrounded by the biocompatible polymer via the layer of bonding agent 22 or the assembly of layers of bonding agent 22'. As can be seen in FIG. 7c, the second surface region is orientated facing the upper side 18 of the base plate 17. Clearly, it is also possible and advantageous for the layer of bonding agent 22 or the assembly of layers of bonding agent 22' to provided both at a third surface region 24 which is opposite to the second surface region 23 and/or at the upper and/or lower sides 18 and 19 of the base plate 17.

The number and arrangement of the individual structural elements 20 may be selected in any manner. However, geometrically arranged configurations KO are preferably used such as, for example, square, pentagonal, hexagonal or higher patterns, as can be seen in FIG. 7b.

FIGS. 8a-8f illustrate a cuff M which partly surrounds the support substrate 1 of the implantable cuff electrode CE, which comprises the region of the support substrate 1 on both its lower and upper sides which are directly attached to the support substrate region 1B and which, in contrast to the support substrate 1B, are not deformed themselves, by inherent mechanical pretensioning, into a right cylinder, and thus are positioned flush with the epineurium of the nerve fiber bundle when implanted in position.

The cuff M acts first of all to improve handling of the implantable cuff electrode CE which, because of its very small support substrate thickness and also the very fine wired electrode assemblies positioned on the support substrate surface, demands very careful handling by the operator. The cuff M is preferably designed to be in one piece and is provided with a lower cuff portion Mu as well as an upper cuff portion Mo which are both connected together via a film hinge 25. See FIGS. 8b and 8c in this regard. The lower cuff portion Mu is provided with a depression 26 for embedding the support substrate 1, into which the support substrate 1 can be inserted. When inserted, the lower cuff portion Mu surrounds the support substrate 1 in the manner shown in FIG. 8b, that is the lower cuff portion Mu protrudes out laterally from beneath the support substrate 1.

The upper cuff portion Mo, which is connected as one piece with the lower cuff portion Mu via the hinge joint 25, matches the shape and size of the lower cuff portion Mu. Like the lower cuff portion Mu, upper cuff portion Mo is provided with a depression 27 so that when closed, the cuff M hermetically surrounds the support substrate in the manner shown in FIG. 8a, wherein only the support substrate region 1B protrudes out of the cuff M.

In addition to the improved handling, the cuff M in particular also acts to improve fixing of the cuff electrode CE relative to the nerve fiber bundle. In this regard, the upper cuff portion Mo and lower cuff portion Mu are each provided with fastening openings 14'. See FIGS. 8a, 8b and 8d which are aligned with the fastening openings 14 positioned within the support substrate 1 when the cuff M is folded up. In this manner, it is possible to pass a surgical suture 28 through the openings 14 and 14' of the cuff electrode CE surrounded by the cuff M. In this manner, the fastening opening 14, surrounded by the metallic ring of the cuff electrode CE, can be relieved by the fastening opening 14' introduced into the cuff M. Preferably, the cuff M is produced from a stable plastic material and for example from parylene. To increase the strength further, Mo and Mu may be a polymer hybrid, for example parylene (inner) and silicone rubber (outer). This hybrid has the advantage that the stability of the parylene is combined with the tear strength of the silicone. In a preferred embodiment, the fastening openings 14' within the cuff M are reinforced by an appropriate thickening of the material.

Window openings 29 are introduced into the upper cuff portion Mo which ensures free access to the reference electrode contacts 12. FIG. 8e shows a cross-section in this regard through the support substrate 1 surrounded by the cuff M, on the upper side of which reference electrode contacts 12 are located, which remain freely accessible because of the window openings 29 within the upper cuff portion Mo. Preferably, the window openings 29 surround the reference electrode contacts 12 with a steeply inclined border flank 29', so that this ensures that the entire surface of the reference electrode contacts 29 can come into face-to-face physical contact with the surrounding tissue.

Figure 8A:
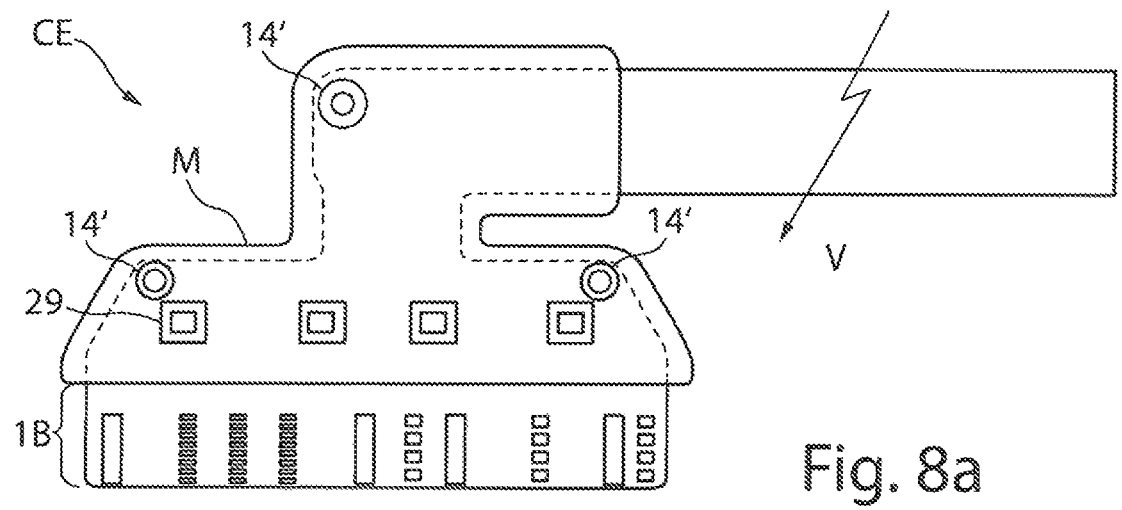
FIG. 8a-f illustrate an additional reinforcing cuff for the implantable electrode assembly.
Figure 8B:
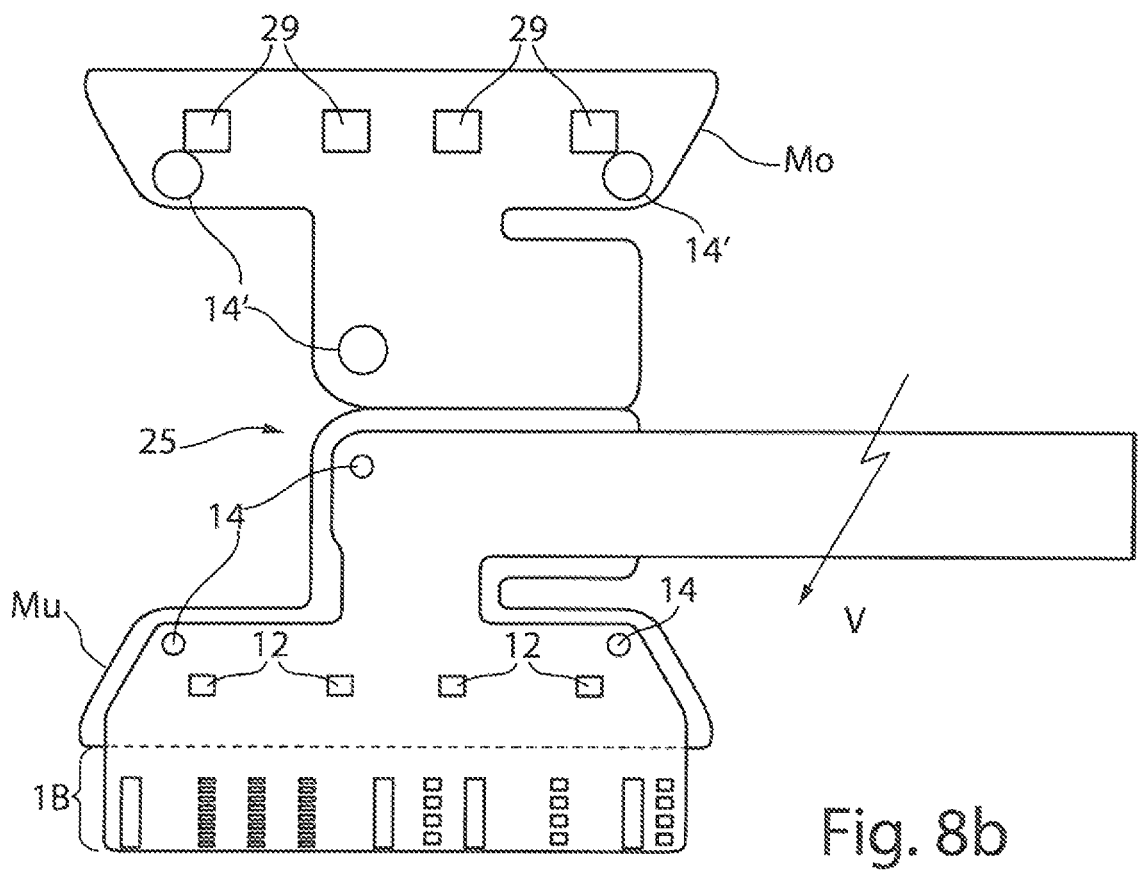
Figure 8C:
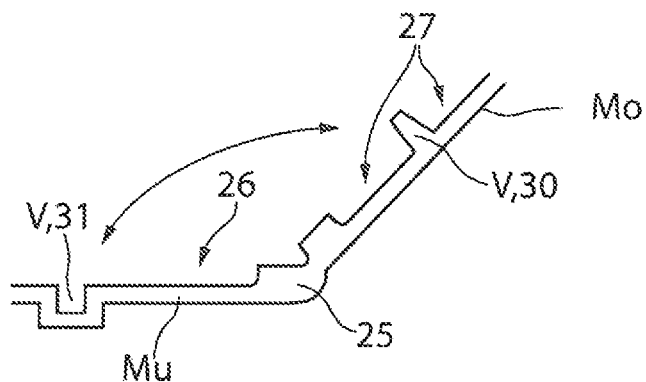
Figure 8D:
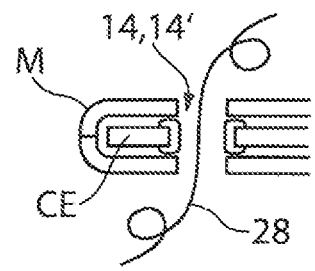
Figure 8E:
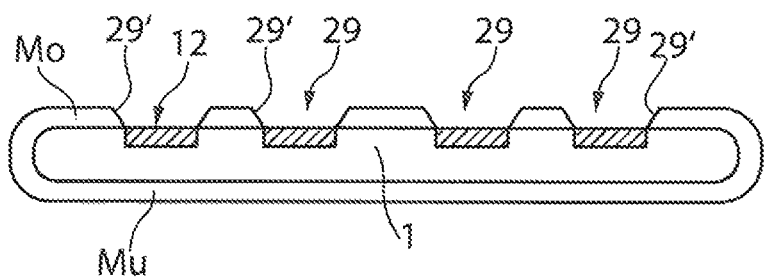
Figure 8F:
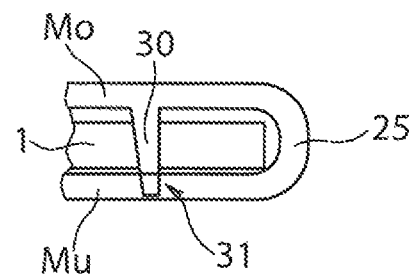

In order to ensure that the cuff M remains closed, locking structures V are disposed between the upper cuff portion Mo and lower cuff portion Mu which, for example, are a pin 30 and an opposing recess 31 as shown in FIGS. 8c and 8f. When the upper cuff portion and lower cuff portion are brought together, the pins 30 are urged into contact with the corresponding recess 31 in which the respective pin 31 is permanently retained by friction. FIG. 8f illustrates a locked structure V. Here, the pin 30 on the upper cuff portion Mo protrudes through a corresponding opening in the support substrate 1 and its end sits within the recess 31 of the lower cuff portion Mu. Clearly, alternative embodiments may be utilized for the locking structures as for example in the form of suitably formed latching mechanisms.

Figure 9:
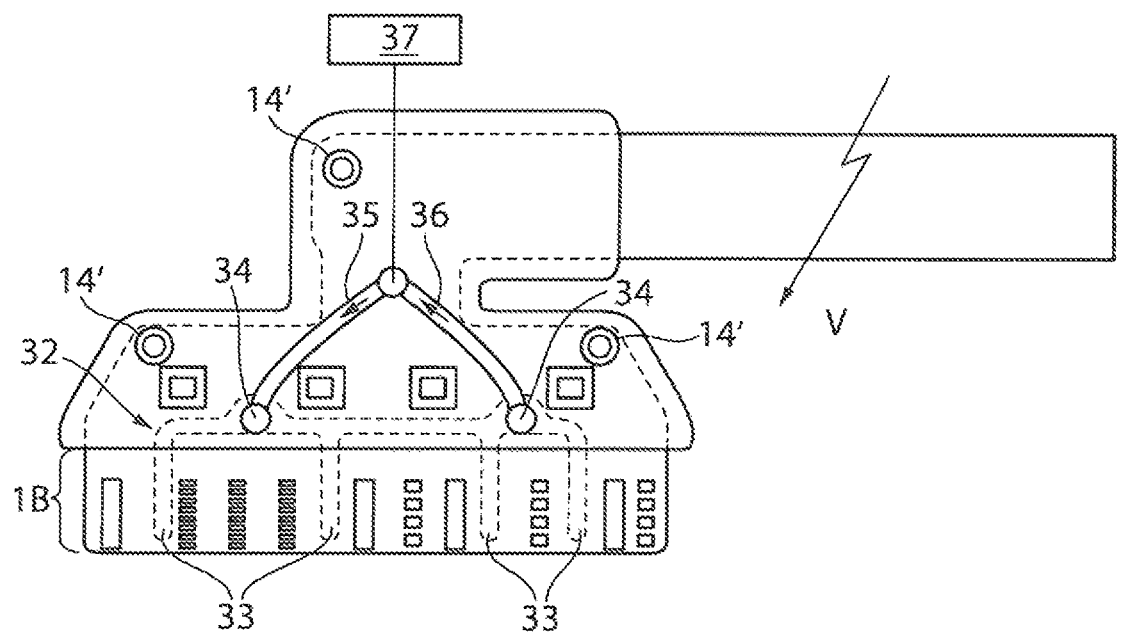
FIG. 9 shows a hydraulic application structure for the implantable electrode assembly.

FIG. 9 illustrates a further embodiment which allows the cuff electrode CE in accordance with the invention to be implanted more easily. Within the support substrate 1 is a fluid channel system 32 which is completely surrounded by the support substrate 1. The fluid channel system 32 essentially extends in the region of the support substrate region 1B which, because of inherent pretensioning of the material, takes on the shape of a right cylinder by rolling itself up. If, on the other hand, the fluid channel system 32 is filled with a fluid, preferably water, then the water pressure applied along the fluid channel system flattens out the support substrate region 1b against the inherent rollup force of the material. In this regard, the fluid channel system 32 is provided with fluid channel branches 33 running in the circumferential direction of the sleeve surface of the self-shaping right cylinder. When filled, they force the support substrate region 1B to extend as required.

At least two channel openings 34 within the support substrate 1 are provided in order to fill the fluid channel system 32. Their sizes and configurations are determined such that they open in a fluid-tight manner at entry and exit openings within the fluid supply or removal lines 35 and 36 running inside the cuff M. The supply or removal lines 35 and 36 running inside the cuff M are connected fluidically with a fluid control system 37 which can be actuated by an operator.

In the event of implantation, the fluid channel system 32 is filled with a fluid, whereupon the support substrate region 1B is extended. When in this state, the operator places the cuff electrode CE precisely at a predetermined site along the nerve fiber bundle. Next, the fluid channel system 32 is emptied by the operator, whereupon the support substrate region 1B winds itself around the nerve fiber bundle. In the final step, a surgical suture is passed through the fastening openings 14' of the cuff in order to fix the cuff electrode CE to the surrounding tissue.

In an advantageous embodiment of the above fluid channel system 32, it may be filled with a shape memory metal or polymer. For the purposes of activation, the channel openings 34 are provided with metallic contacts via which an electrical voltage can be applied along the supply lines 35 and 36 to unfold the implantable electrode assembly CE via an appropriately modified control device 37, until the electrodes are eventually in position.

Figure 10:
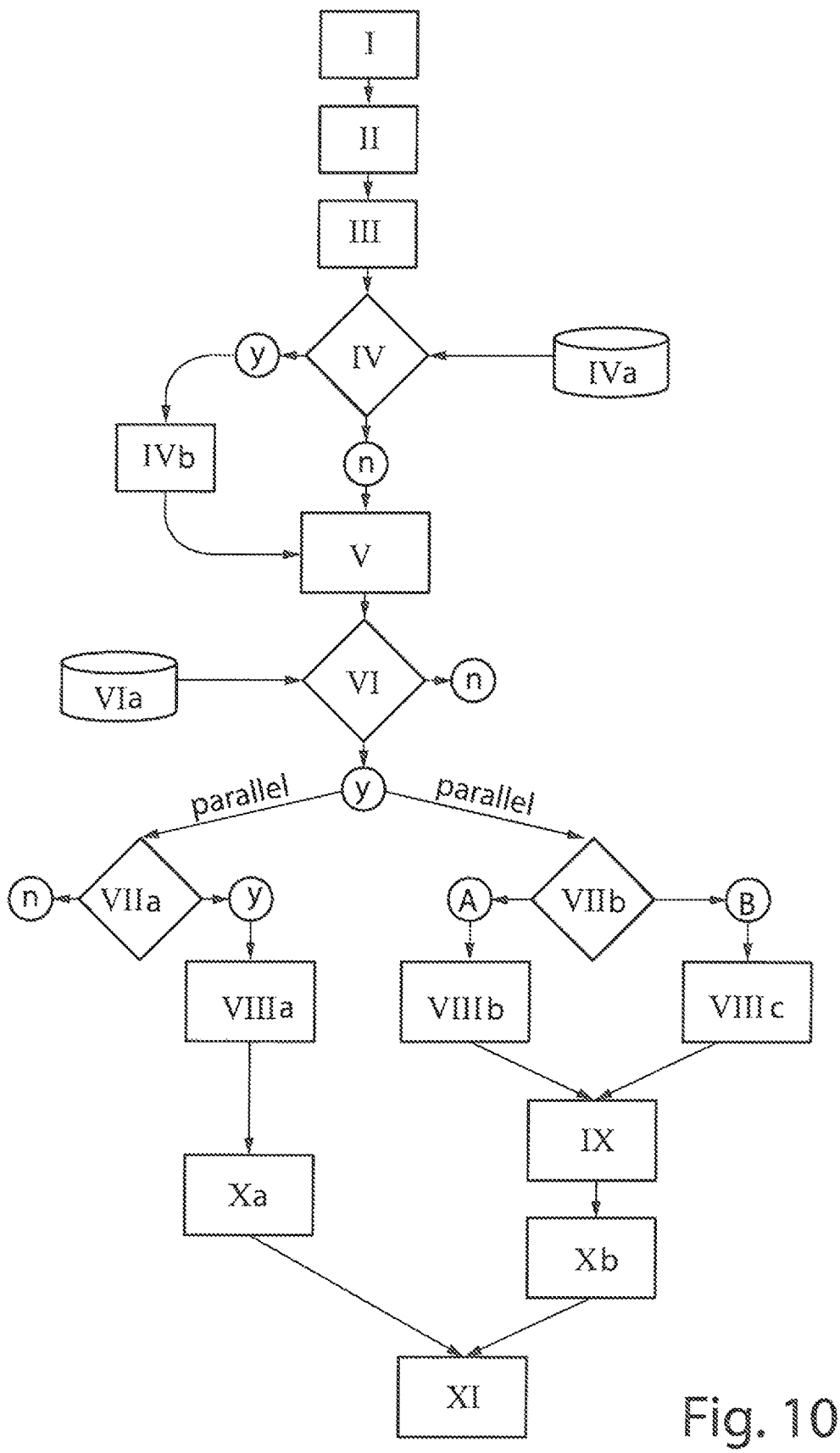
FIG. 10 shows a flow diagram for carrying out the electrical stimulation of a nerve fiber.

FIG. 10 illustrates a flow diagram which shows the sequence of individual steps for blood pressure manipulation or regulation by selective electrical stimulation of nerve fibers. It should be assumed that for the purposes of the stimulation, the electrode assembly shown in FIG. 6 has been applied locally around the vagus nerve so that the inhibition function is possible. If inhibition could be eliminated, then the electrode assembly of FIG. 2*a* is also suitable. The discussion below also refers to the components of the implantable assembly E shown in FIG. 1. In order to avoid repetition, it should be noted that the decision points marked with "y" denote "yes" and those with "n" denote "no".

I) Start: activation of implantable assembly E either manually or automatically and the analysis and control unit in the form of a microcontroller is initiated (A/S. FIG. 1).

II) Acquisition of ECG signal using the electrodes 12 of the cuff electrode E as seen in FIG. 6. The analysis and control unit A/S validates the R wave and separates any EMP errors out of the signal, wherein a plurality of runs are monitored. The analysis and control unit A/S then determines the reliability with which the rzs can be detected. Finally, the analysis and control unit A/S determines the heart rate.

III) Acquisition of blood pressure signal SN using the first electrode contacts 4, the first electrode strips 5 as well as the ECG electrode contacts 12 of the cuff electrode E. This is carried out by coherent averaging of the signals from the middle row of the first electrode contacts 4 triggered by the rising flank of the ECG signal which has already been determined.

IV) Decision as to whether a change in blood pressure is present.

IVa) Here, the analysis and control unit A/S queries an up-to-date reference blood pressure (SB) and compares or calibrates the amplitude of the reference signal with the blood pressure signal SN.

IVb) Validation of the blood pressure and the stimulation position, if a change in blood pressure is present. See y. The analysis and control unit/A/S asks the Lookup table LT for blood pressure signal values SN already stored for this patient as well as time intervals ZV and ZV* and compares them with the blood pressure signal SN acquired by averaging. The analysis and control unit A/S determines the "best" SN of an electrode, this is tagged as the forthcoming stimulation electrode in the working memory.

V) Determination of the temporal delay ZV between the ECG signal and blood pressure reference signal. Here, the comparator unit K1 determines the temporal delay between the R wave and rising threshold and reference blood pressure.

The comparator unit K2 determines the temporal delay ZV* between the rising threshold of the reference signal and the neuronal blood pressure signal acquired by the electrode. See ZS in FIG. 3 and SN in FIG. 4. The start P1 and end P2 of the pulse wave PW are determined from the reference blood pressure. This interval produces T1. See FIGS. 3B and 3C. The interval T1 is delayed by the temporal offset ZV+ZV* and provides the interval ZF as shown in FIG. 3.

VI) Decision as to stimulation and selection of stimulation parameters. The analysis and control unit A/S determines the time UH and the actual position and movement of the patient using the accelerometer BS. The analysis and control unit A/S also determines the impedances of the stimulation electrode via the interstimulus impedance detector. Based on the blood pressure values, the heart rate, the activity of the patient and lack of any other contrary control commands that are obtained, as for example triggered by an external signal by the radio comms module (SES), an error function signal for a component of the implant (for example an IC of the stimulation side), or the detection of a strong statistical magnetic field (EMP), etc, the analysis and control unit A/S decides whether stimulation should be carried out—yes (y) or no (n).

VIa) Stimulation reference values. The analysis and control unit A/S compares the parameters obtained with those already stored in the Lookup table LT and the storage module SM and selects appropriate stimulation parameters ("appropriate" means how "strong" and how "long" stimulation must be carried out in order to reduce the blood pressure by x %).

The stimulation coordinates such as ZF, the number and form of the pulses are communicated to the "activating" function generator F1 (binary). If selective inhibition has to be carried out at the same time, the appropriate stimulation parameters for selective inhibition are communicated to the function generator F2 (binary).

VIIa) The analysis and control unit A/S decides upon the inhibition method (HF or anodal block).

VIIb) The analysis and control unit A/S decides upon the stimulation mode A or B (See FIG. 5).

VIIIb) Preparation/modulation of activating stimulation parameters in accordance with mode A:
If mode A is selected for a rapid intervention, a fixed stimulation sweep with a defined number of individual pulses is prepared (the duration is not correlated with the ZF interval, but taken from a table), which is repeated with predetermined breaks. See FIG. 5, mode A.
The analysis and control unit A/S transmits a template to the first function generator F1, which generates the voltage signal which is transmitted to the modulator M1.

VIIIc) Preparation/modulation of activating stimulation parameters in accordance with mode B:
If mode B is selected, the individual pulses have to be optimized further. The first function generator F1 produces an analogous template of a stimulation interval (SSI) and fits a specific number of individual biphase pulses into the interval ZF. In this regard, the stimulation signal is matched to the biological signal. The reference blood pressure profile is laid over the amplitude of the individual pulse as an envelope function. See FIG. 4A. The first function generator F1 transmits the table with the prepared stimulation sweep to the modulator M1.

IX) Matching the phases of the individual pulses of the sweep:
The modulator M1 is responsible for both modes and varies the two phases of each individual pulse. See FIG. 4B in order to produce an ideal individual pulse form for the individual patient. The modulator M1 transmits the "prepared" voltage signal in the form of a sweep to the signal-current converter (SSW1).

Xb) Carrying out the activating stimulation:
The signal-current converter SSW1 waits for the ECG trigger signal and waits until the "active window for stimulation ZF" is reached and transmits the stimulation sweep to the previously selected stimulation electrode. Between each individual pulse, the impedance of the stimulation contact is recorded by the electrode impedance measurement unit EM. If a polarization is detected by the analysis and control unit A/S, it gives the active polarization comparator EE1 the order to supply a small extra charge between each pulse through the stimulation contact as compensation. If this inter-stimulation compensation is insufficient, then in addition, after ending the sweep, the intersweep compensator is activated and compensates for any polarization.

VIIIa) Preparation/modulation of the inhibiting stimulation parameters:

The analysis and control unit transmits a stimulation interval for the inhibition to the function generator F2. As a rule, this is longer than the activating stimulation, that is it begins shortly before and ends after the activating stimulation.

The analysis and control unit A/S establishes whether the second function generator F2 should apply an anodal block, that is only a monophase block, or whether HF blocking should be carried out. The function generator 2 also produces a stimulation (voltage) template. In the event of an HF block, F2 transmits the voltage signal to the modulator M2 in order to "smooth" the individual phases.

Xa) Carrying out the inhibiting stimulation:

The signal-current converter SSW2 converts the signal, either as an anodal block of the F2 or as a HF block of M2, into a current signal and feeds it via the inhibition electrode 9 of the array 13 as seen in FIG. 6. The electrode impedance measurement unit EM monitors the polarization of the inhibiting electrodes 9 and if necessary activates the depolarization unit EE2 via the analysis and control unit A/S to provide compensation.

In the case of an HF block, both can occur, interstimulus and intersweep. In the case of anodal block, only the intersweep compensator is active.

XI) Analysis of stimulation:

The analysis and control unit A/S determines the change in the blood pressure curve and introduces a repetition. In the case of mode B, as a primary stimulation parameter, the number of heartbeats the stimulation covers can be varied. By means of this function, (patient-specific) feedback of the mode of operation of the implant is carried out.

The outcome of the stimulation is written into the memory so that it can be used for subsequent comparisons.

| List of reference numerals | |
|---|---|
| 1 | support substrate |
| 1' | support substrate surface |
| 1B | support substrate region |
| 2 | first electrode assembly |
| 3 | first electrode structures |
| 4 | first electrode contacts |
| 4a | axial extent of first electrode contacts |
| 4U | extent of first electrode contacts in circumferential direction |
| 5 | first electrode strips |
| 6, 6' | signal detector and generator |
| 7 | third electrode assembly |
| 8 | third electrode strip |
| 9 | third electrode contacts |
| 9a | axial extent of third electrode contacts |
| 9U | extent of third electrode contacts in circumferential direction |
| 10 | optical waveguide assembly |
| 11 | optical waveguide openings |
| 12 | second electrode assembly, ECG electrode contacts |
| 13 | third electrode structure |
| 14 | fastening openings |
| 15 | opening |
| 16 | electrode strip surface |

-continued

| List of reference numerals | |
|---|---|
| 17 | base plate |
| 18 | upper side |
| 19 | lower side |
| 20 | structural element |
| 21 | surface region |
| 22 | layer of bonding agent |
| 22' | assembly of layers of bonding agent |
| 23 | second surface region |
| 24 | third surface region |
| A | axial direction |
| A/S | analysis and control unit |
| A3, A4 | amplitudes |
| $A_{max}$ | maximum amplitude |
| AT | rising signal portion |
| BS | accelerometer |
| de | dip |
| E | implantable electrode assembly, cuff electrode |
| E1 | anodic amplitude |
| E2 | cathodic amplitude |
| E3 | cathodic pulse width |
| E4 | anodic amplitude |
| E5 | repetition rate |
| E6 | repolarization flank |
| E7 | break, zero level between anodic and cathodic amplitude |
| EE1, EE2 | depolarization unit |
| ECG | ECG time signal |
| EM | electrode impedance measurement unit |
| EMP | unit for protection against electromagnetic pulses, EMP and MRT |
| EP | individual pulse |
| ES | energy storage and energy source |
| F1, F2 | function generator |
| g | brain |
| H | heart |
| KO | geometric configuration |
| KT | cathodic signal portion |
| L | conductor |
| LA | longitudinal axis of structural element |
| LI | optic fiber |
| LQ | light source(s) |
| LT | Lockup table |
| M | maximum |
| M1, M2 | modulator |
| NF | nerve fiber |
| NFB | nerve fiber bundle |
| P1, P2 | characteristic phase points along time signal |
| PW | pulse wave, blood pressure wave |
| R | R wave of ECG signal |
| SB | blood pressure sensor |
| SES | signal and energy supply unit |
| SM | storage module |
| SN | natural neuronal electrical signal |
| SSI | stimulation signal |
| SSW1, SSW2 | signal-current converter |
| T | timer unit |
| T1 | duration of pulse wave |
| $T_{SN}$ | pulse duration of a natural neuronal electrical signal |
| U | circumferential direction |
| UH | clock |
| V | connecting structure |
| ZF | time window |
| ZS | time signal |
| ZV, ZV* | time delay |

The invention claimed is:

1. A method for locationally selective acquisition of neuronal electrical signals which propagate along at least one nerve fiber contained in a nerve fiber bundle of a living human or an animal organism and for selective electrical stimulation of the at least one nerve fiber, and in which a brain of a human or an animal does not distinguish between neuronal electrical signals and electrical stimulation signals, the method comprising:

acquiring neuronal electrical signals propagating along an afferent nerve fiber at a selected location;

generating electrical signals with a signal duration and temporal amplitude profile corresponding to the acquired neuronal electrical signals;

modifying the generated electrical signals by raising or reducing amplitude thereof at least within a temporal region of the electrical signals to obtain electrical stimulation signals;

applying the electrical stimulation signals to the afferent nerve fiber in a temporal phase with the neuronal electrical signals; and applying at least one electrical inhibition signal to the afferent nerve fiber temporally before and during application of an electrical stimulation signal to the afferent nerve fiber, so that the electrical stimulation signal only propagates unidirectionally along the at least one nerve fiber.

* * * * *